United States Patent [19]
Kraus et al.

[11] Patent Number: 5,746,741
[45] Date of Patent: May 5, 1998

[54] EXTERNAL FIXATOR SYSTEM

[75] Inventors: Karl H. Kraus, Sutton; George E. Chu, Westford; Brian J. Rollins, Bellingham; Harold M. Wotton, III, Fiskdale; Danielle L. Luongo, Tyngsboro, all of Mass.; Donald M. Kallio, Jr., Barrington, R.I.; Bryan E. Cotton, Watertown; David P. Brooks, II, Framingham, both of Mass.

[73] Assignees: Tufts University, Medford; Worcester Polytechnic Institute, Worcester, both of Mass.

[21] Appl. No.: 643,512

[22] Filed: May 6, 1996

[51] Int. Cl.$^6$ ................................................ A61B 17/56
[52] U.S. Cl. .............................. 606/54; 606/53; 606/56; 606/61; 606/73
[58] Field of Search ................... 606/61, 73, 72, 606/59, 56, 151, 54, 53, 104

[56] References Cited

U.S. PATENT DOCUMENTS

| | | | |
|---|---|---|---|
| 2,372,866 | 4/1945 | Tofflemire | 606/59 |
| 2,391,537 | 12/1945 | Anderson | 606/59 |
| 2,391,693 | 12/1945 | Ettinger | 606/59 |
| 4,628,919 | 12/1986 | Clyburn | 128/92 |
| 5,002,542 | 3/1991 | Frigg | 606/61 |
| 5,098,432 | 3/1992 | Wagenknecht | 606/59 |
| 5,207,676 | 5/1993 | Canadell et al. | 606/54 |
| 5,275,599 | 1/1994 | Zbikowski et al. | 606/54 |
| 5,292,322 | 3/1994 | Faccioli et al. | 606/59 |
| 5,304,177 | 4/1994 | Pennig | 606/58 |
| 5,312,403 | 5/1994 | Frigg | 606/54 |
| 5,314,426 | 5/1994 | Pohl et al. | 606/58 |
| 5,320,622 | 6/1994 | Faccioli et al. | 606/58 |
| 5,320,623 | 6/1994 | Pennig | 606/59 |
| 5,342,360 | 8/1994 | Faccioli et al. | 606/59 |
| 5,350,378 | 9/1994 | Cole et al. | 606/57 |
| 5,391,167 | 2/1995 | Pong et al. | 606/57 |
| 5,393,161 | 2/1995 | Mata et al. | 403/133 |
| 5,397,322 | 3/1995 | Campopiano | 606/57 |
| 5,476,462 | 12/1995 | Allard et al. | 606/61 |

FOREIGN PATENT DOCUMENTS

| | | | |
|---|---|---|---|
| 194187 | 9/1986 | European Pat. Off. | 606/56 |
| 0 707 832 A1 | 4/1996 | European Pat. Off. | |
| 91 03 480.9 | 7/1991 | Germany | |
| 638 390 | 9/1983 | Switzerland | |

OTHER PUBLICATIONS

Ebix Fix, DynaFix™ System, DFS™ Standard Fixator, Operative Technique, Brochure.(No Date Given).

D.P. Brooks, Jr., et al., "Design of a Fastener and Bolt for an External Fixation Device," *Worcester Polytechnic Institute*, submitted in partial fulfillment of the requirements for the Degree of Bachelor of Science, pp. 1–69 (Apr. 28, 1994).

G. Chu, et al., "External Skeletal Fixation," *Worcester Polytechnic Institute*, submitted in partial fulfillment for the Degree of Bachelor of Science, pp. 1–109 (May 1, 1995).

Synthes Price List 1995, *Synthes* (USA) P.O. Box 1766, 1690 Russell Road, Paoli, PA 19301-0800 (Aug. 1992) (Brochure).

Slatter, D., "*Textbook of Small Animal Surgery,*" Second Edition, Volume II, pp. 1641–1660 (1995, 1985 by W.B. Saunders Company).

*Primary Examiner*—Michael Buiz
*Assistant Examiner*—Julian W. Woo
*Attorney, Agent, or Firm*—Hamilton, Brook, Smith & Reynolds, P.C.

[57] ABSTRACT

An external fixator system comprises a clamp adapted to couple a fixator pin to a connecting rod. The clamp includes a slot for transversely receiving the body of the connecting rod. The slot preferably includes a region of reduced width, providing interference between the clamp and the connecting rod as it is inserted. This causes the clamp to snap onto the rod. A bolt is inserted through a hole passing through both sides of the slot. The bolt includes a head at one end formed in the shape of a hook adapted to hook the shaft of a fixator pin, and a thread at the opposite end. The bolt is rotatably mountable in the hole such that the fixator pin can be retained at a range of angles relative to the connecting rod. The clamp is attachable to a fixator pin and a connecting bar between two previously-installed clamps without disassembly of the system.

39 Claims, 18 Drawing Sheets

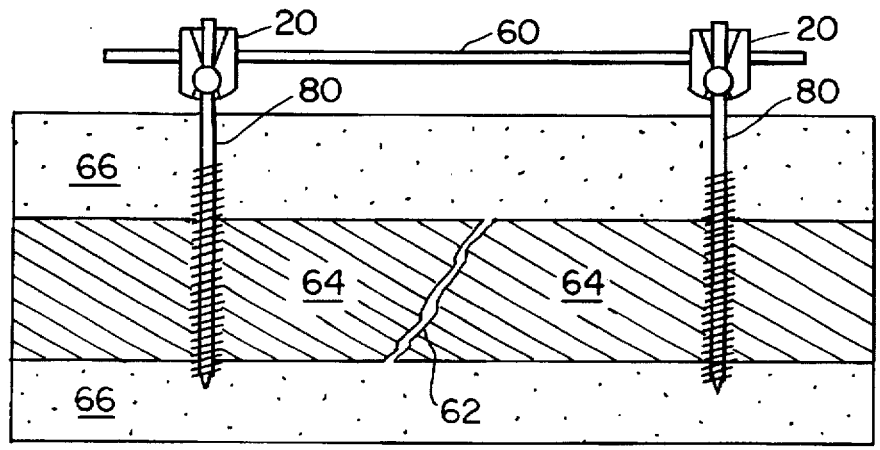
FIG. 8A
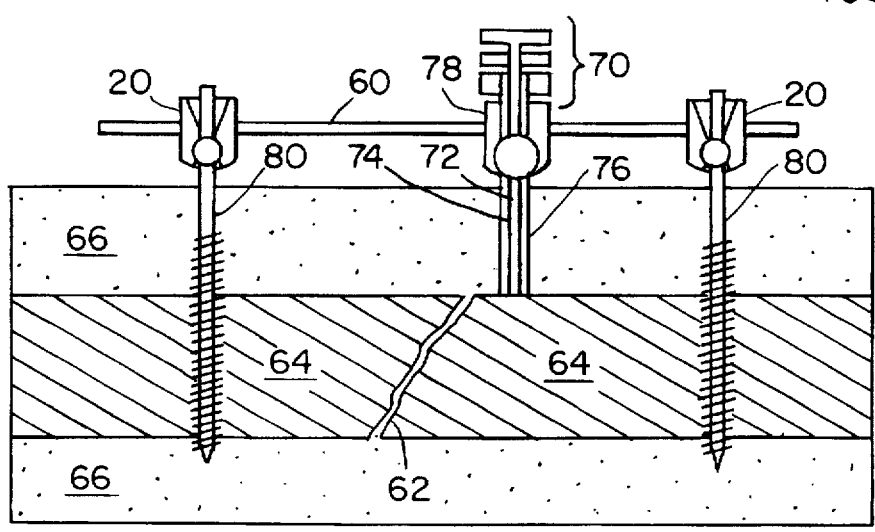
FIG. 8B'
FIG. 8B
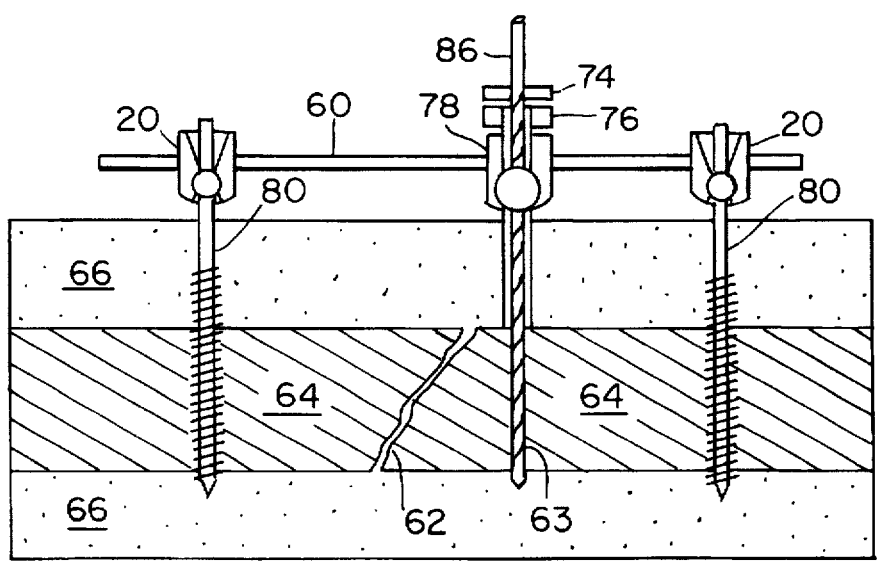
FIG. 8C

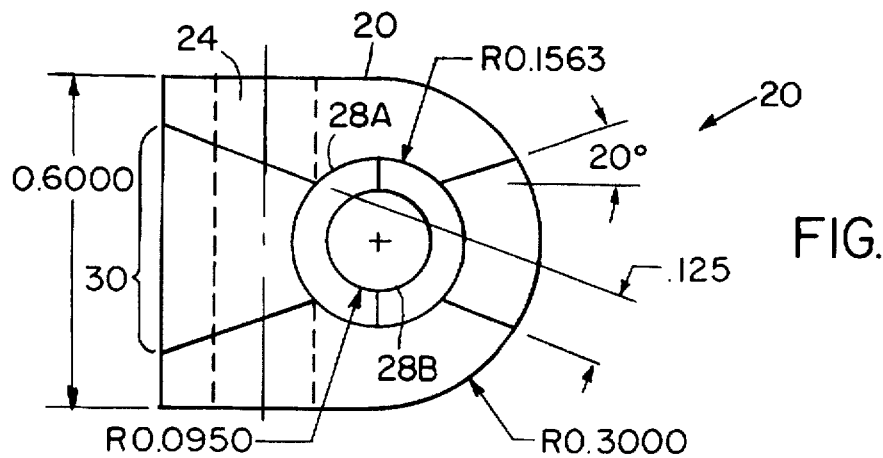
FIG. 11A
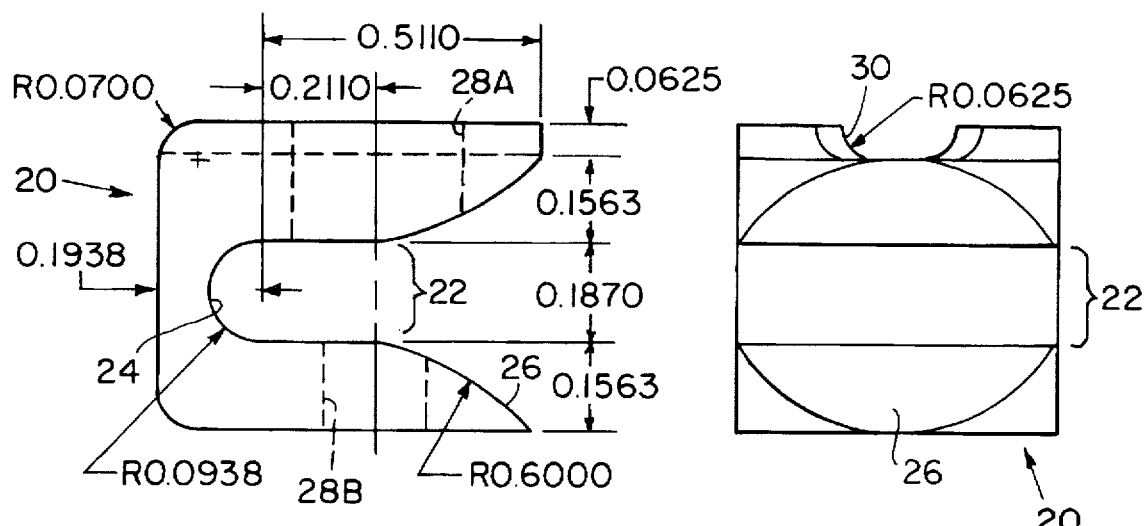
FIG. 11B
FIG. 11C
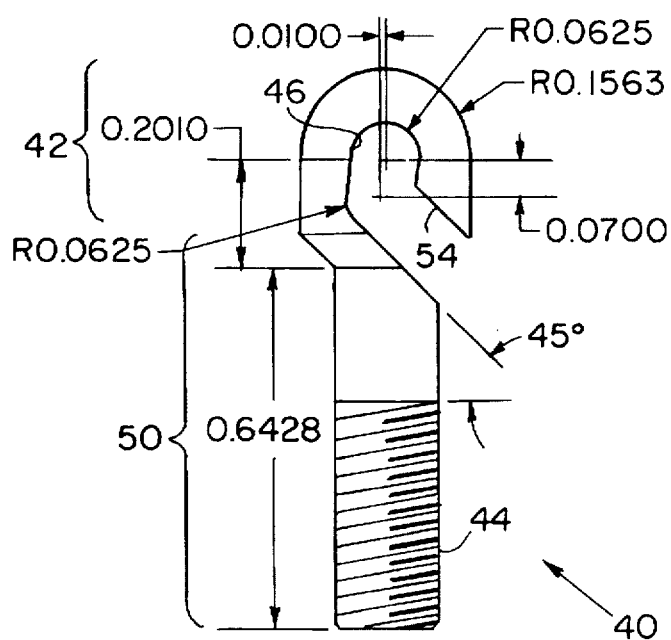
FIG. 11D

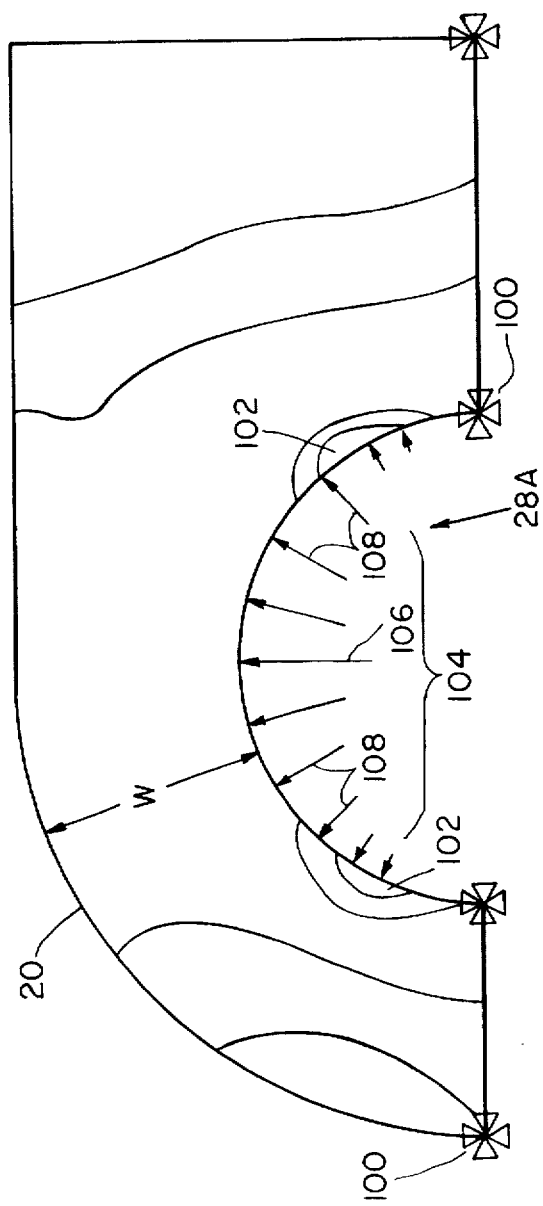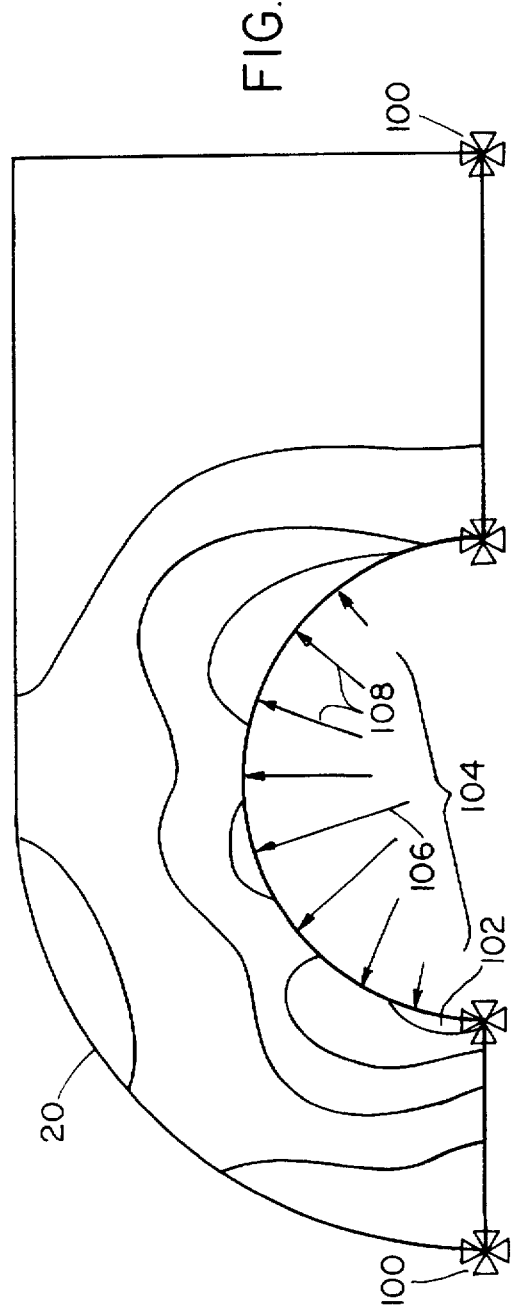

EXTERNAL FIXATOR SYSTEM

BACKGROUND OF THE INVENTION

Skeletal fixation devices immobilize fractured bones or joints during osteosynthesis. Conventional fixation methods include casting and internal fixation. In a casting procedure, the injured limb is wrapped in a plaster or fiberglass shell in the proximity of the fracture. In an internal fixation procedure, pins are drilled into the bone at various angles to stabilize the fracture. While conventional fixation methods are adequate for treating simple fractures, they are insufficient for treating more serious injuries involving multiple or compound fractures. External skeletal fixation is the method of choice for treating these complex injuries.

In modern external fixator systems, a plurality of pins are drilled through a patient's skin and into a fractured bone. Clamps secure the pins to a common connecting rod, creating a rigid frame for immobilizing the fracture to enable healing. External skeletal fixation is the preferred method of treatment for various limb deformities and wounds including: severe open fractures; fractures associated with severe burns; fractures requiring subsequent crossleg flaps, free vascularized grafts, or other reconstructive procedures; fractures requiring distraction; limb lengthening; arthrodesis; infected fractures; nonunions. External fixation offers several advantages over conventional fixation methods. It enables skeletal stabilization away from the proximity of injury, disease, or deformity. This allows for direct surveillance of the limb and wound for primary or secondary procedures: dressing changes; skin grafting; irrigation. Alignment of the fracture, length, compression, and fixed distraction are adjustable following initial surgery. Minimal interference with proximal and distal joints enables immediate mobilization of the wounded limb. An extremity can be elevated without placing pressure on posterior soft tissue. Insertion of the fixator pins can be performed under local anesthesia.

The most extreme stresses occur at the pin-bone interface, which could lead to premature loosening. It is therefore important to select pins of maximum stiffness. As pin stiffness is proportional to the fourth power of pin radius, positive-profile threaded pins are preferred. A positive-profile threaded pin has threads of greater diameter than the pin shaft, resulting in a stiffer pin and increased pin-bone adhesion. These are preferred over negative-profile threaded pins which have threads cut into the shaft, and therefore have drastically reduced pin stiffness.

The Kirschner-Ehmer external fixator is commonly used in veterinary orthopedic surgery. System elements include: a standard connecting rod; clamps adapted to slide over the ends of the connecting rod; fixator pins for insertion into bone tissue; bolts for securing the pins to the clamps and for tightening the clamps around the connecting bars. The bolt includes a hole for receiving a fixator pin shaft. To maintain proper rigidity, the bolt hole diameter is designed to be nearly equal to the pin shaft diameter. This precludes insertion of a positive-profile threaded pin through the bolt hole. Consequently, use of positive-profile threaded pins requires pin insertion into the bone before alignment with the bolt head and tightening of the clamp. While it is possible to place positive-profile threaded pins in the most proximal and most distal locations on the connecting rod, addition of such pins in other locations is difficult. This presents a serious surgical complication for applications requiring several pins.

In addition, the Kirschner-Ehmer system precludes installation of an additional clamp between two installed clamps on the connecting bar or removal of a clamp therefrom without disassembly of the entire fixator. This is because the Kirschner-Ehmer clamp includes a narrow slot leading to a wider channel into which a connecting rod is inserted axially. The connecting rod will not fit into the slot to allow for transverse mounting. Consequently, the surgeon must anticipate the number of clamps required and position them on the connecting bar before insertion of the end pins into the bone. This is especially limiting if an additional pin or clamp is required at the completion of surgery or at subsequent patient visits.

In the Kirschner-Ehmer system, pins are placed through the clamp and then drilled into the bone through unprotected skin and soft tissue. The pins have sharp trochar spade points to aid in placement. These points do not efficiently or cleanly drill through bone, leading to soft tissue or bone damage. In addition, the Kirschner-Ehmer clamp undergoes plastic deformation when tightened, permanently deforming and fatiguing the material. Consequently, reuse of the clamp is discouraged. Furthermore, the Kirschner-Ehmer clamp is inapplicable in ring fixators such as the Ilizarov external ring fixator.

A fixator clamp produced by Synthes™ permits transverse installation of a clamp on a connecting bar between two installed clamps without disassembly. It includes a slot for receiving a connecting bar, a hole for receiving a pin in an orthogonal direction relative to the connecting bar, a clevis-shaped clamp, and a bolt and nut which simultaneously secure the pin in the hole and the clamp on the connecting bar. This design is limited to orthogonal pin placements relative to the connecting bar and is mechanically complex. Furthermore, the pin hole is designed to receive the pin shaft rather than the thread, precluding insertion of positive-profile pins.

The Synthes™ and Kirschner-Ehmer designs are particularly susceptible to loosening under repeated cyclic loading. The Kirschner-Ehmer device relies entirely on the axial tension in the bolt to preclude pin rotation. A slight amount of loosening due to cyclic loading reduces axial tension in the bolt, allowing the pin to rotate relative to the connecting rod. The Synthes™ design relies on a clamp which touches the connecting bar at only two points, rendering this device susceptible to loosening. Furthermore, both clamp designs are compatible only with pins of a single diameter.

SUMMARY OF THE INVENTION

The present invention is directed to an external fixation apparatus and method which overcome the various limitations of the prior art devices. The apparatus of the invention includes an external fixator clamp adapted to couple a fixator pin to a connecting rod.

In one aspect of the apparatus of the invention, the clamp includes a slot which receives a connecting rod. The slot has a region of reduced width. The reduced-width region provides interference between the clamp and a transversely-inserted connecting rod. This causes the clamp to snap onto the rod, the clamp temporarily deforming to accommodate the rod as the rod interfaces with the slot in the region of reduced width. Coupling means secure a fixator pin to the clamp.

In another aspect of the apparatus of the invention, the clamp includes a slot having a channel at its base for receiving a connecting rod, a hole passing through the slot, a bolt, and a nut. The bolt includes a head at one end formed in the shape of a hook and adapted to transversely hook the shaft of a fixator pin, and the bolt has a thread at the opposite end. The bolt inserts through the hole, retained by the fixator pin at the head and secured by the nut at the thread.

In another aspect of the apparatus of the invention, the clamp includes a slot for transversely receiving the body of the connecting rod, a hole passing through the slot, a bolt, and a nut. The bolt includes a head at one end adapted to receive a fixator pin, and a thread at the opposite end. The bolt inserts through the hole, retained by the fixator pin at the head and secured by the nut at the thread. The bolt is rotatably mounted in the hole such that the fixator pin can be retained at a range of angles relative to the connecting rod.

In a preferred embodiment of the invention, torque induced on the nut generates tension in the bolt between the nut and fixator pin. The tension in the bolt corresponds to a compressive force operating across the clamp, causing the clamp to deform. This causes a reduction in the width of the slot, clamping the connecting rod in the base of the slot. With elastic deformation, the spring force of the clamp serves to lock the nut and fixator pin to prevent loosening, and permits reuse of the clamp.

The bolt head preferably includes a hook having a lip adapted to wrap about the shaft of a fixator pin. When the nut is tightened, the lip deforms about the fixator pin, causing the lip to exert a continuous outward force against an inner surface of the hole. The deformation produces an interference fit in the hook operating on the hole. This serves to lock the hook in the hole to prevent loosening due to torsional loading on the bolt caused by cyclical fixator pin loading. The hook deformation is preferably plastic so that maximal outward force is applied by the lip on the inner surface of the hole. For the minor cost of nonreusability of the bolt due to plastic deformation, the coupling strength is greatly increased.

Alternatively, the bolt head may include a hole for slidably receiving the end of the fixator pin. A tapered hole would allow the bolt to receive a range of pin diameters. In either case, the holed bolt head preferably deforms around the fixator pin in the same manner as the hooked bolt head, generating a continuous outward force on the bolt hole for locking the bolt in place.

In another aspect of the invention, an instrument is provided for installing a fixator pin. The instrument comprises an installation clamp having a slot for transversely receiving a connecting rod. A cannula is slidably mounted on the clamp and inserted through soft tissue to a bone surface. The cannula provides access to the bone for insertion of a fixator pin therethrough, while protecting soft tissue from being torn or burnt by the fixator pin.

In a preferred embodiment of the instrument adapted for safe insertion of positive-profile threaded pins, the cannula comprises an inner cannula inserted through an outer cannula. The inner cannula diameter corresponds to the shaft diameter of the positive-profile pin and the outer cannula diameter corresponds to the thread diameter of the pin. A trochar is slidably inserted in the cannula for advancing the cannula through soft tissue to the bone surface. The trochar is removed and a drill inserted into the inner cannula for drilling a pilot hole in the bone corresponding to the pin shaft diameter. The drill bit and inner cannula are removed, and a depth gauge may be inserted through the cannula and into the bone for measuring the width of the bone at the pilot hole. A positive-profile threaded pin is cut to the appropriate length and threaded into the hole while the outer cannula protects soft tissue from interfering with the pin. Following pin insertion the outer cannula is removed, and the installation clamp is replaced by a standard pin-connecting clamp as described above.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 8A–8F are sectional side views of a tooling sequence for alignment, insertion and placement of a fixator pin in accordance with the present invention.

FIG. 8B' is a close-up view of the pin placing tool comprising a trochar, an inner cannula and an outer cannula in accordance with the present invention.

FIG. 11A includes top, side, and front dimensional views of a preferred embodiment of the clamp in accordance with the present invention.

FIG. 11B is a dimensional side view of a preferred embodiment of the bolt in accordance with the present invention.

FIG. 16A is a diagram of the forces operating on the bolt hole and the resultant stresses induced in the clamp for a pin mounted perpendicular to the connecting rod.

FIG. 16B is diagram of the forces operating on the bolt hole and the resultant stresses induced in the clamp for a pin mounted 20° off center.

DETAILED DESCRIPTION OF THE PREFERRED EMBODIMENT

The external fixator system of the present invention enables external fixation of orthopedic fractures in humans and animals. The primary component of the present invention is a clamp which couples a fixator pin to a connecting rod. The clamp is adapted to transversely receive the body of the connecting rod. Consequently, the clamp can be installed on the connecting rod between previously-mounted clamps without disassembly of the entire system.

The present invention further comprises a bolt and nut which secure the fixator pin to the clamp and which secure the clamp to the connecting bar. The bolt preferably includes a hook which allows the pin to be mounted to the clamp without having to slide the bolt over the end of the pin shaft. This feature renders the present invention applicable for use with positive-profile threaded pins, and with pins of a range of shaft diameters. The bolt is preferably adapted to deform plastically within the bolt hole, providing increased resistance to cyclical pin loading, and increased multi-dimensional stability. The clamp can be reused, as it is adapted to deform elastically during mounting on the connecting bar and during tightening.

The system described herein is well-suited for use with instrumentation for alignment and pre-drilling of pin holes, depth measurements, and pin coupling. The instrumentation includes a cannula for protecting soft tissue during drilling and mounting, thereby increasing patient safety during installation procedures.

Figure 1:
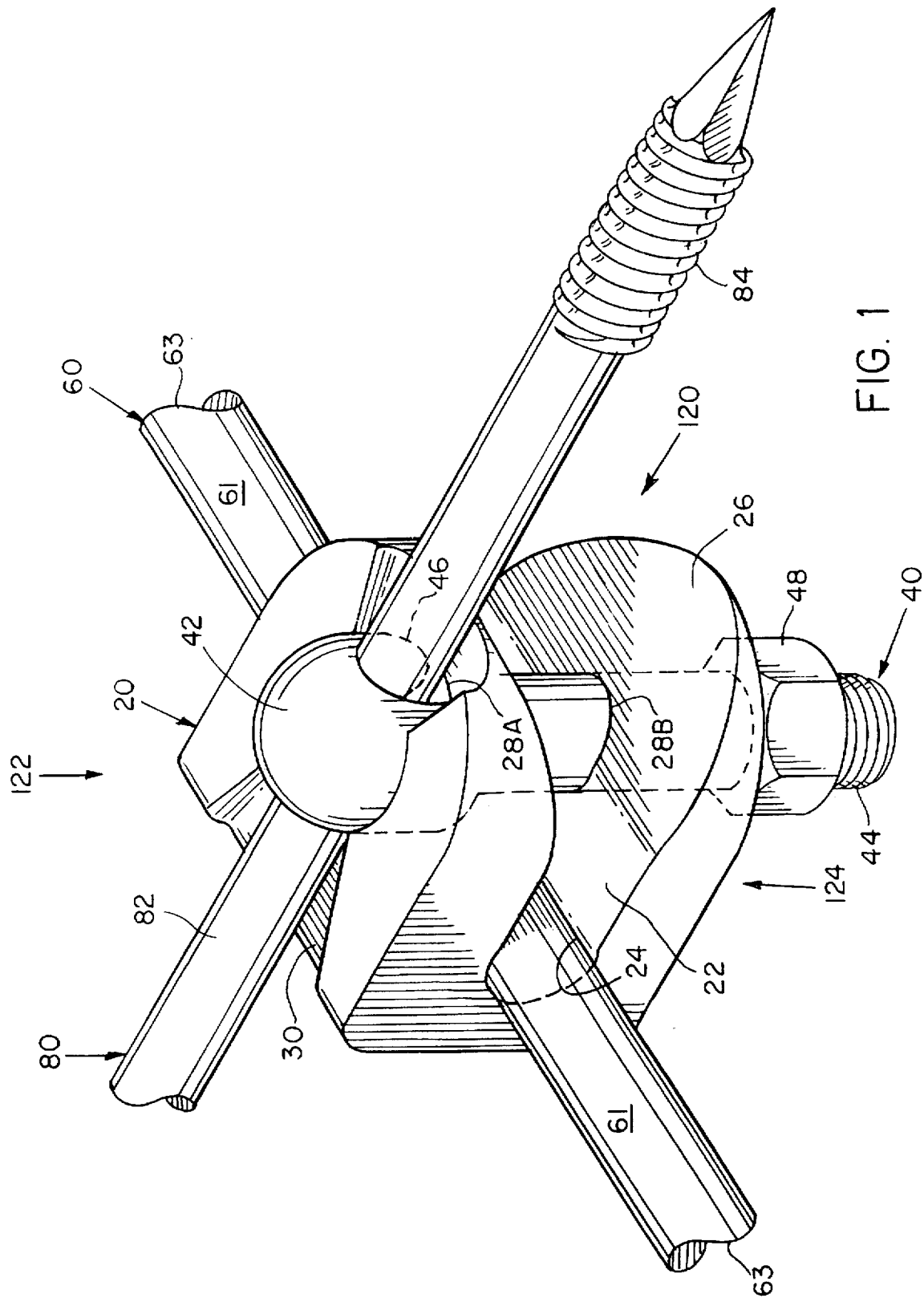
FIG. 1 is a perspective view of a fixator clamp coupled to a connecting rod and fixator pin in accordance with the present invention.

FIG. 1 is a perspective view of a fixator system in accordance with an embodiment of the present invention. The system includes a clamp 20, a bolt 40, and a nut 48. The clamp 20 is adapted to snap onto a connecting rod 60 having a body 61 and two ends 63. To accommodate the connecting rod 60, the clamp includes a slot 22 extending from a channel 24 at the slot base to a front side 120 of the clamp 20. The channel 24 width is substantially equal to the diameter of the connecting rod 60, and the width of the slot 22 is slightly less than the channel width, so that when the body 61 of the connecting rod 60 is transversely inserted into the slot opening 26, it interferes with the slot 22. Force is required to insert the rod 60 deeper into the slot 22, until the connecting rod 60 reaches the channel 24 at which point it snaps into place. The force of the connecting rod 60 operating on the slot 22 causes the clamp 20 to spread open and receive the rod 60. Maximum deformation occurs when the connecting rod 60 is disposed at the interface between the slot 22 and the channel 24. Similar force is required to reverse the process and remove the clamp 20 from the connecting rod 60.

A hole 28A, 28B passes transversely through the slot 22 to accommodate a bolt 40. The bolt 40 includes a head 42 on a proximal end and a thread 44 on a distal end. The bolt hole 28A is larger on the top side of the slot 22 to receive the bolt head 42. The lower hole 28B is smaller and receives the bolt thread 44.

The bolt head 42 is adapted to communicate with and secure a fixator pin 80. The bolt thread 44 interfaces with a nut 48. The bolt 40 inserts through the bolt holes 28A, 28B after the clamp 20 is snapped onto the connecting rod 60. A hook 46 on the bolt head 42 slides over the shaft 82 of the fixator pin 80. The fixator pin 80 and the nut 48 jointly secure the bolt in the clamp 20. As the nut 48 is tightened, the bolt head 42 is forced further into the hole 28A, securing the fixator pin 80 against the top surface 122 of the clamp 20. Forces generated between the fixator pin 80 and the nut 48 are translated to the clamp 20. As bolt tension increases due to additional torque on the nut 48, the clamp 20 begins to deform. This causes a reduction in the channel 24 width, which causes the clamp 20 to tighten about the connecting rod 60, securing the rod 60 in the clamp 20. The deformation generates a continuous spring force in the clamp which operates on the fixator pin 80 and the nut 48, serving to lock them in place.

Figure 2:
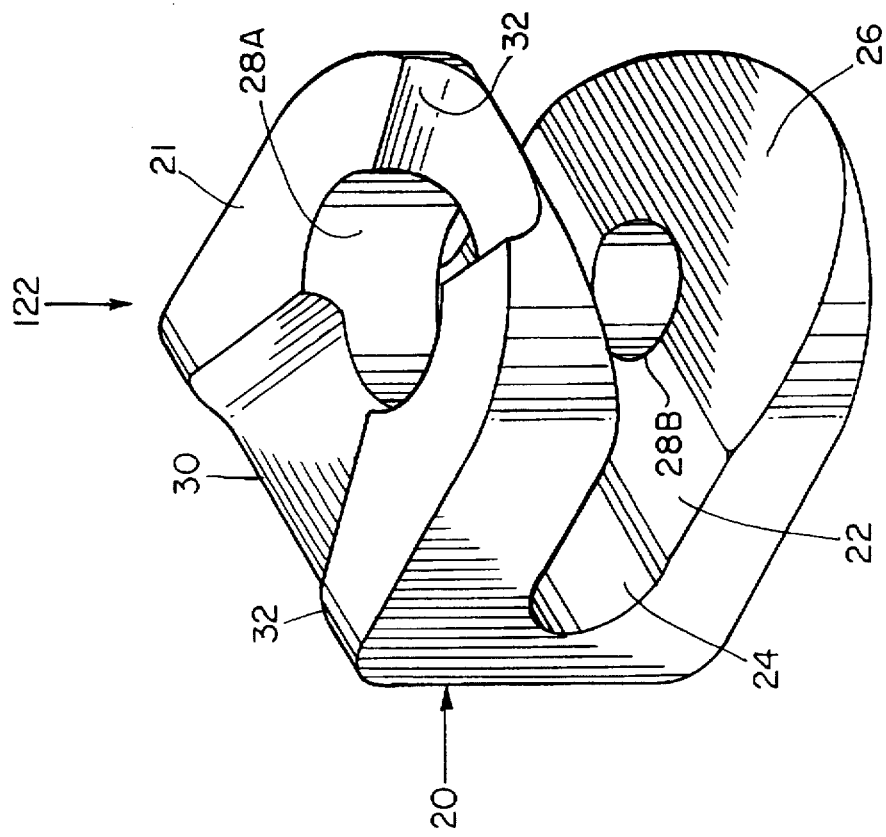
FIG. 2 is a perspective view of the fixator clamp of FIG. 1 in accordance with the present invention.
Figure 18B:
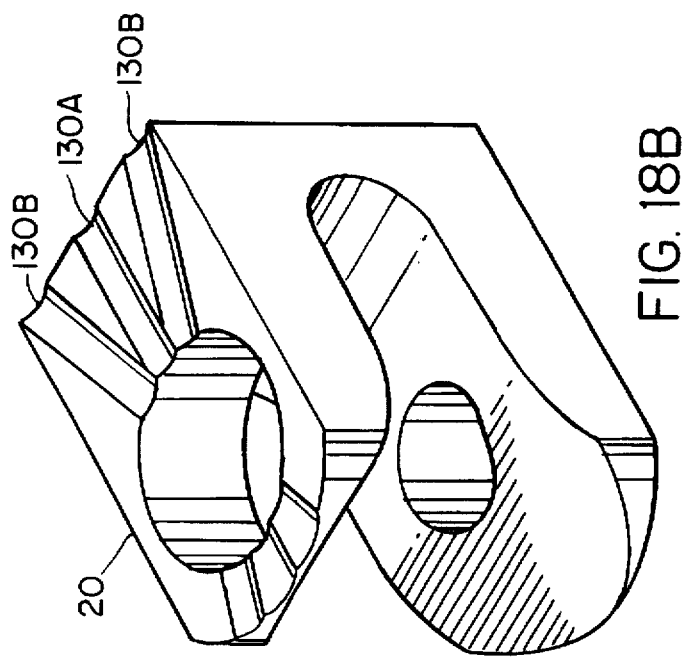
FIG. 18B is a perspective view of an alternative clamp embodiment having a plurality of discrete grooves in accordance with the present invention.
Figure 18A:
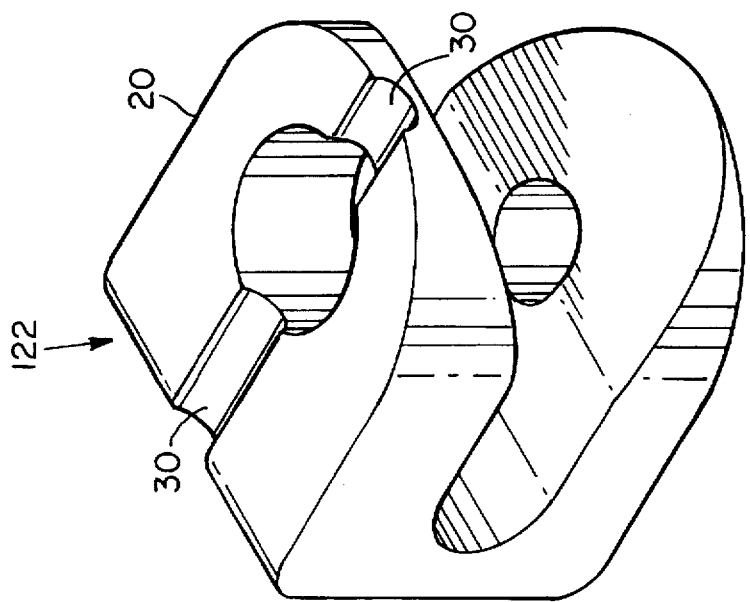
FIG. 18A is a perspective view of an alternative clamp embodiment having a single groove for orthogonal pin placement in accordance with the present invention.

FIG. 2 is a perspective view of the fixator clamp 20. In this view, it is apparent that the top hole 28A is larger in diameter than the bottom hole 28B. This is because the top hole 28A accommodates the wider bolt head 42 and the bottom hole 28B accommodates the thread 44 and body of the bolt. The top surface 122 of the clamp 20 includes a groove 30 adapted to accommodate the fixator pin as shown in FIG. 1. The groove 30 permits angular pin placements within a limited range defined by the side walls 32. The side walls 32 prevent the pin from rotating beyond a particular angle (20° in the embodiment shown), thus strengthening the pin placement when the clamp is tightened with the pin against the wall 32. Alternatively, the clamp may include no grooves or discrete grooves at a variety of angles as shown in FIGS. 18A and 18B.

Figure 3:
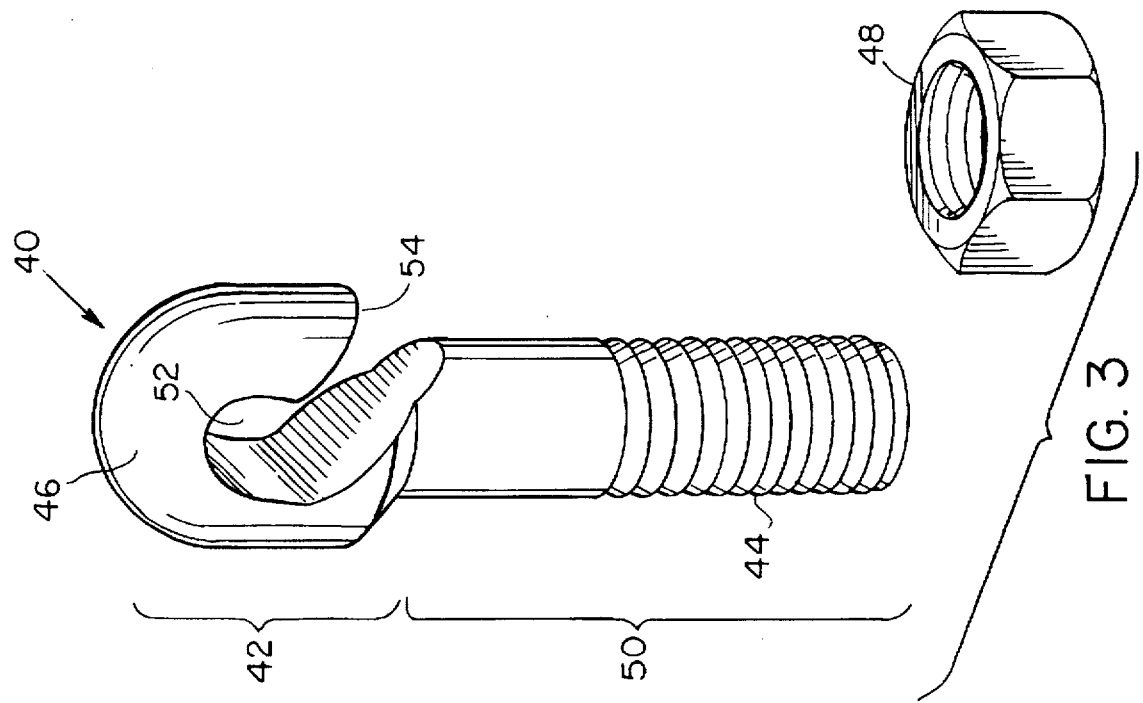
FIG. 3 is a perspective view of the clamp bolt of FIG. 1 in accordance with the present invention.

FIG. 3 is a perspective view of a preferred embodiment of a clamp bolt 40. The bolt includes a head 42 and a body 50. The body 50 includes a thread 44 for receiving a nut 48. A groove 52 is cut into the head 42, forming a hook 46 for receiving a fixator pin 80 as shown in FIG. 1. The hook 46 includes a lip 54 which deforms plastically as torque is applied to the nut 48. This will be described in further detail below.

Figure 4A:
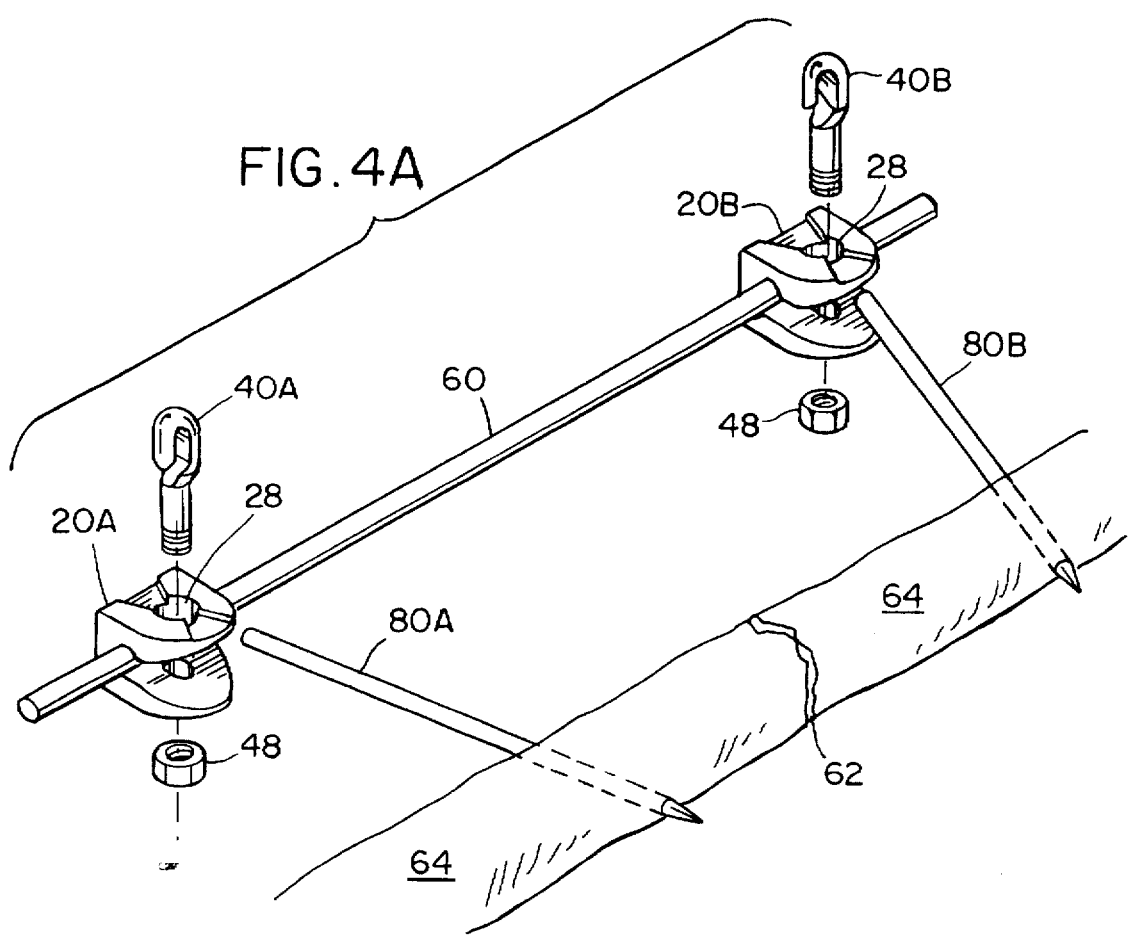
FIG. 4A and 4B are perspective views of a fixation system before and after assembly, respectively, in accordance with the present invention.
Figure 4B:
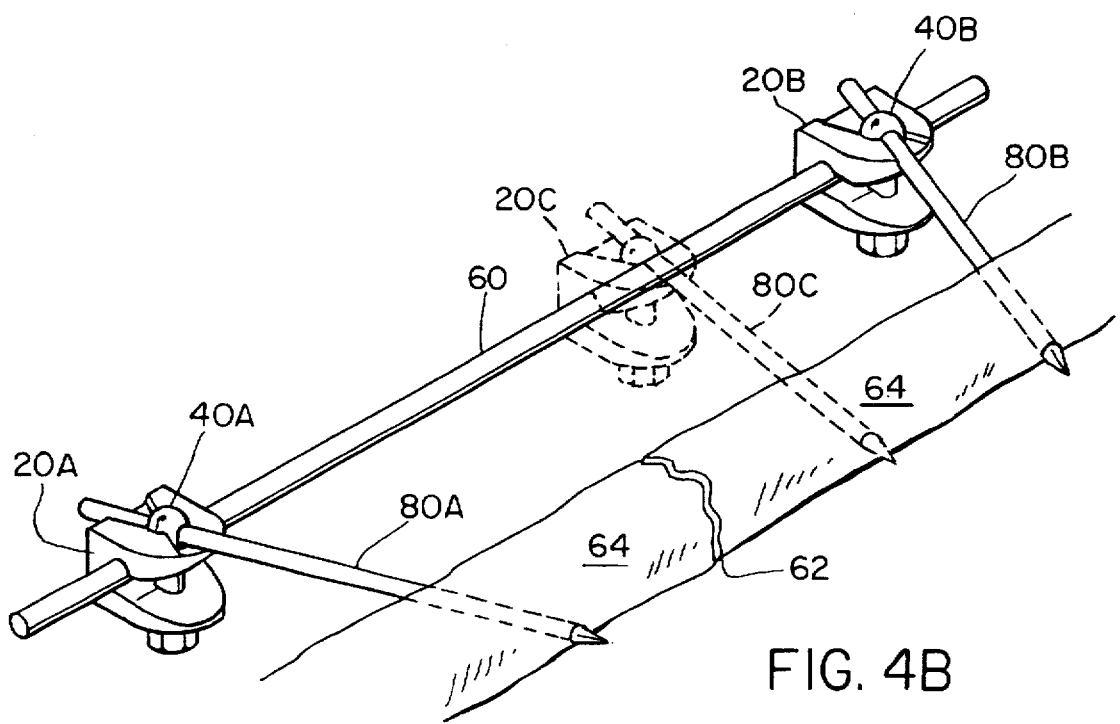

FIGS. 4A and 4B are perspective views of system assembly in accordance with the present invention. Pins 80A,80B are inserted into a bone 64 on each side of a fracture 62 as shown in FIG. 4A. Clamps 20A, 20B are snapped onto the connecting rod 60 for each pin 80A, 80B and are slid into position on the rod to align with the pins. Next, a bolt 40A is hooked around the pin shaft 80A, and the bolt 40A is fed into the bolt hole 28 in the clamp and hand-tightened with a nut 48.

After the first clamp 20A is positioned and hand-tightened, the second clamp 20B is moved into position near the second pin 80B and the second bolt 40B is hooked around the pin 80B and secured by the nut 48. After the nuts are fully tightened, a rigid fixator frame is created as shown in FIG. 4B. With a basic structure, additional clamps 20C and pins 80C may be added to the system and attached to the connecting rod 60 on either side of the fracture 62 as needed. The clamp 20C can be snapped onto the body 61 of the connecting rod at any location on the rod 60 including between the mounted and tightened clamps 20A,20B. This is a significant advantage over the Kirschner-Ehmer clamps which must be slid over the end of the connecting rod 60, and therefore, cannot be attached between two affixed clamps.

Figure 5A:
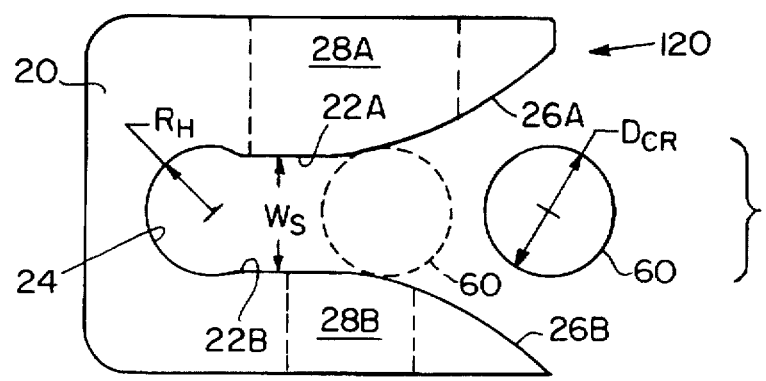
FIGS. 5A–5D are side views of the clamp demonstrating clamp deformation during insertion of a connecting rod.
Figure 5B:
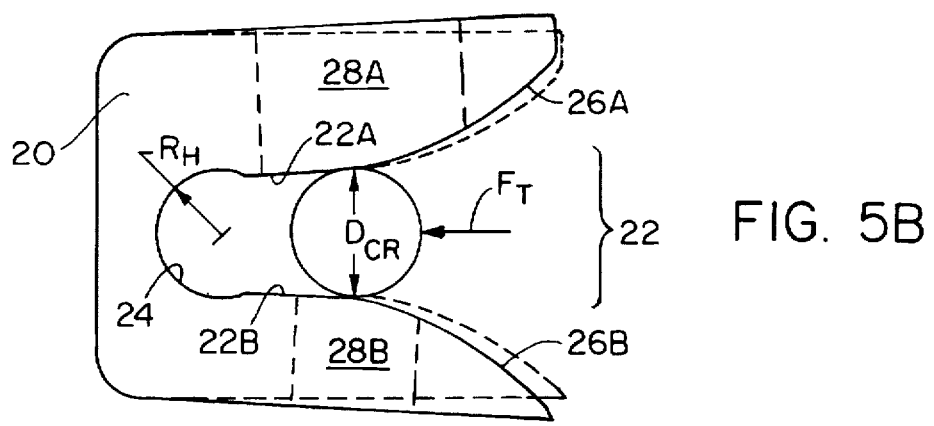

FIGS. 5A–5D are close-up side views of the clamp 20 demonstrating clamp deformation as the clamp 20 is transversely inserted on the body of a connecting rod 60. In FIG. 5A, the clamp 20 includes a semi-cylindrical channel 24 of radius $R_H$. A slot 22 parallel to the channel 24, extends to the front surface 122 of the clamp 20. The slot width $W_S$ is slightly less than the diameter of the channel 24, where the diameter of the channel is equal to the radius $R_H$ multiplied by 2. The faces of the slot 22A, 22B are preferably parallel and preferably neither slot face is tangential to the channel 24. The slot 22 tapers outwardly near its front face 26A, 26B to allow for easy alignment of the connecting rod 60 before insertion.

Figure 5C:
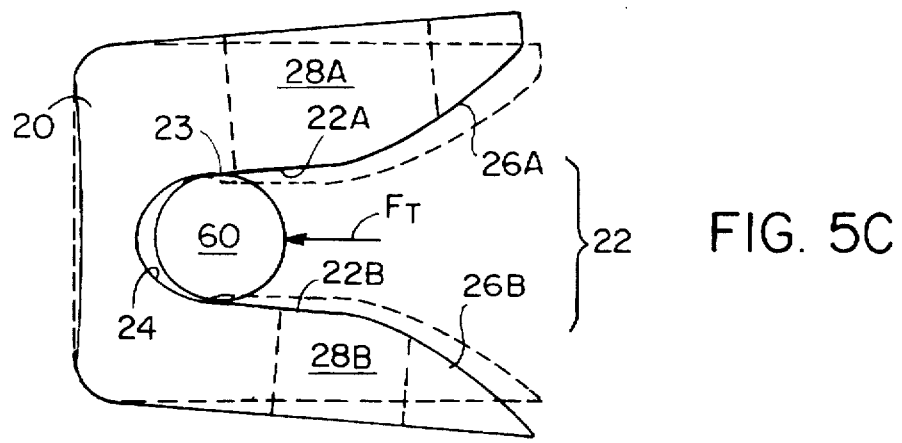

A connecting rod 60 of diameter substantially equal to the channel 24 is transversely inserted into the slot as shown in phantom in FIG. 5A. The connecting rod 60 interferes with the faces of the slot 22A, 22B, and slot openings 26A, 26B because the diameter of the connecting rod $D_{CR}$ is slightly larger than the width of the slot $W_S$. When transverse force $F_T$ is applied to the connecting rod 60, the rod penetrates the slot 22 causing slight deformation in the clamp 20 as shown by the dashed lines in FIG. 5B, which represent the original position of the clamp sides before application of transverse force $F_T$. As the rod 60 is inserted further into the slot 22, the clamp 20 undergoes additional deformation as shown in FIG. 5C. Maximum deformation occurs when the connecting rod 60 is disposed at the threshold of the slot 22 and channel 24, where maximum transverse force $F_T$ is required for further insertion.

Figure 5D:
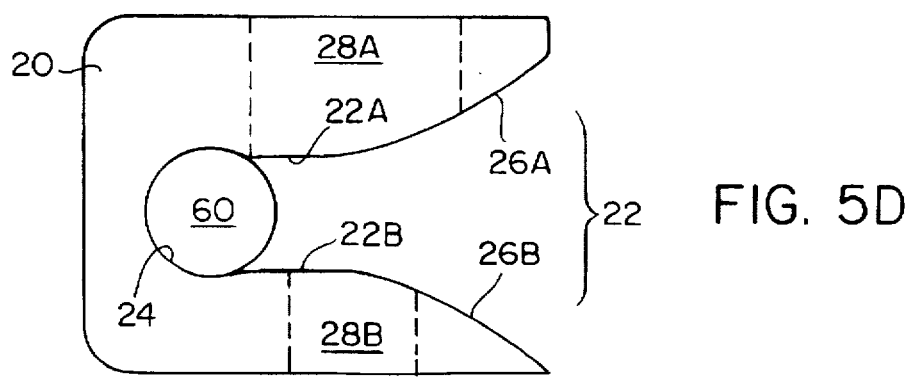

In FIG. 5D, the rod 60 is fully inserted into the slot 22 and snaps into the channel 24. The clamp 20 returns to its original shape, as the slot width $W_S$ is designed to be wide enough so that deformation of the clamp 20 is elastic, rather than plastic. This will be described in further detail below. After the connecting rod 60 is inserted in the channel 24, the clamp 20 is free to rotate about the rod 60 and slide down the body of the rod 60 if the rod 60 diameter is substantially the same as or slightly less than the diameter of the channel 24. For removal, the clamp 20 can be snapped off the body of the rod 60 in a transverse direction opposite that which is described above, or may be slid off the ends of the rod.

Figure 6A:
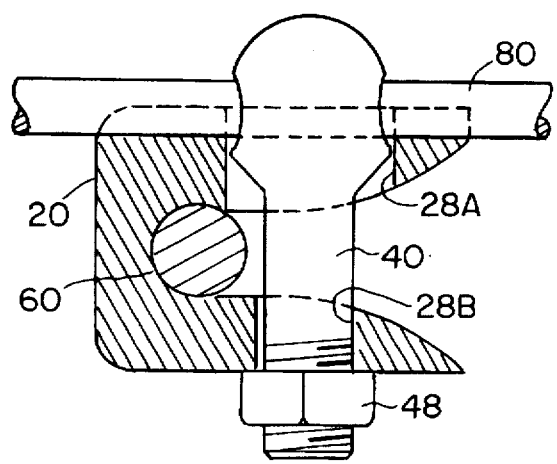
FIGS. 6A–6C are side views of the clamp demonstrating clamp deformation during tightening of the bolt.
Figure 7A:
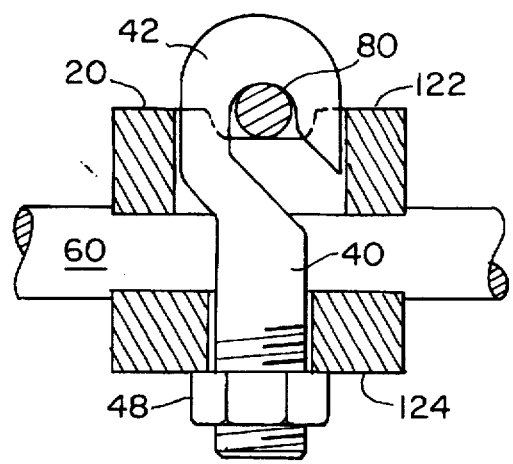
FIGS. 7A–7C are front views of the clamp tightening sequence corresponding to the side views of FIGS. 6A–6C.
Figure 6B:
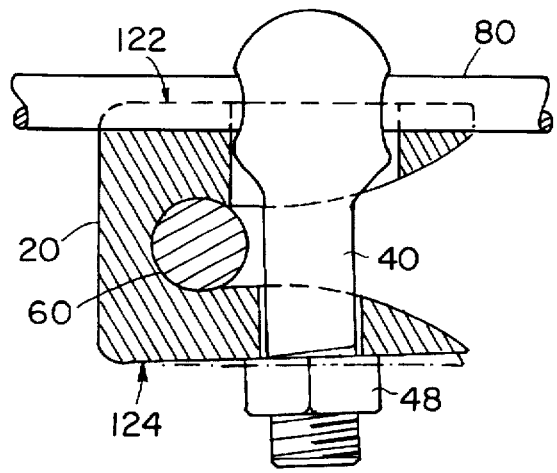
Figure 7B:
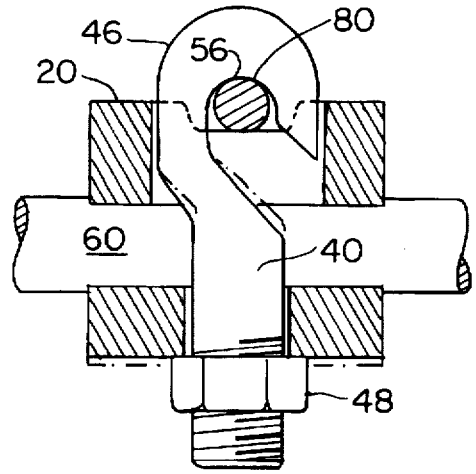
Figure 6C:
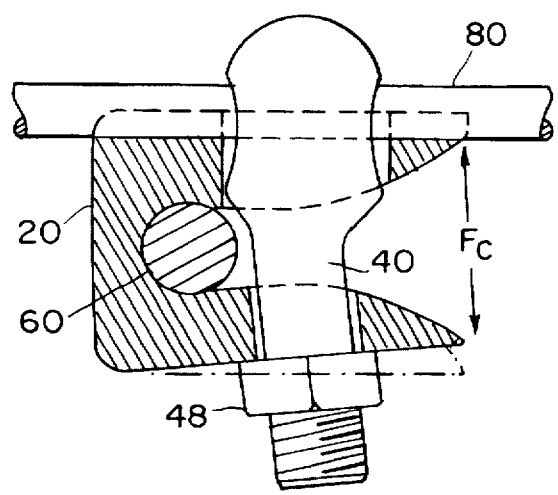
Figure 7C:
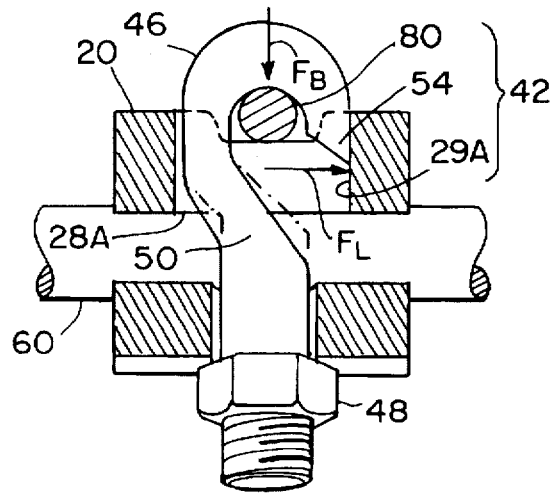

The next steps in the mounting process include securing the pin 80 in the clamp 20 and tightening the clamp 20 about the connecting rod 60. Both steps are accomplished with a single bolt in the present invention as shown in FIGS. 6 and 7. FIGS. 6A–6C are side views of the clamp 20 as the bolt 40 is tightened by nut 48. FIGS. 7A–7C are front views of the tightening sequence corresponding to the side views of FIGS. 6A–6C.

In FIG. 6A, the clamp 20 is snapped onto a connecting rod 60, and a pin 80 is hooked and held in place by a bolt 40 and nut 48 combination, the bolt 40 being inserted through bolt holes 28A, 28B as described above. Corresponding FIG. 7A shows a front view of the clamp 20, connecting rod 60, pin 80, and bolt 40. At this point, there is no torque on the nut 48 and therefore, no downward pressure is exerted on the pin 80 by the bolt head 42.

In FIG. 6B, torque applied to the nut 48 induces tension in the bolt 40 between the pin 80 and the nut 48 on the bottom surface 124 of the clamp 20. This tension causes a slight deformation in the clamp 20 as shown by the dashed lines in FIG. 6B. The tension also forces the underside 56 of the hook 42 down on the pin 80 as shown in FIG. 7B. Further tightening induces additional tension on the bolt 40 which causes the hook 46 to deform.

In FIG. 6C, the nut 48 is fully tightened, placing maximum tension on the bolt 40 between the pin 80 and the nut 48. This causes the clamp 20 to further deform about the connecting rod 60, securing them together. At least 180° of surface area of the channel 24 is in contact with the body of the connecting rod, providing strong contact therebetween. Stresses induced in the clamp 20 due to deformation are preferably within the elastic range of the clamp material so that the clamp 20 is reusable. This will be described in further detail below.

In corresponding FIG. 7C, the hook 46 has undergone further deformation. As the nut 48 is tightened, the body 50 of the bolt 40 is pulled into tension, causing the hook 46 to stretch and deform around the pin 80. The pin 80 is a rigid structure which deforms minimally, if at all. Before tightening, the bolt head 42 is shaped to substantially conform to the shape of the bolt hole 28A in the clamp 20. Because of this, deformation of the hook 46 in the hole 28A causes the lip 54 of the hook 46 to outwardly interfere with the inner wall 29A of the bolt head hole 28A. This interference is in the form of a continuous outward force $F_L$ pushing the inner surface of the hole 28A which operates to lock the bolt head 46 in the hole 28A in the vertical and rotational directions. Thus, the action of torque on a single nut 48 generates tension in the bolt $F_B$ which secures the pin 80 against the clamp 20 and further secures the clamp 20 on the connecting rod 60. Additionally, the force $F_L$ of the deformed hook lip 54 against the wall of the bolt hole 28A provides torsional rigidity of the pin 80 relative to the clamp 20, preventing the pin from rotating in the hole 28A when lateral force is applied to the pin 80. Also, compression of the clamp causes a reactionary force $F_c$ (see FIG. 6C) to operate on the pin 80 and the nut 48 which serves to lock the pin and nut in place. This provides a structure which is more rigid than prior art systems.

Figure 8D:
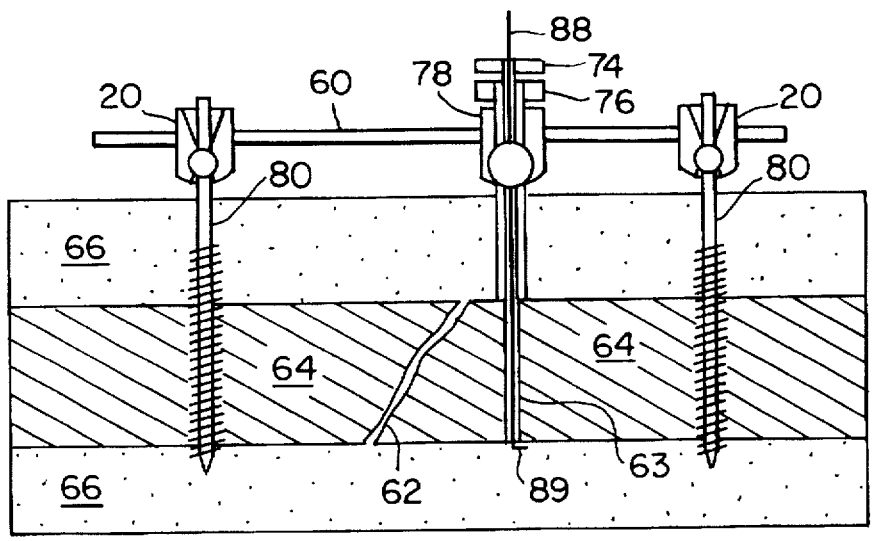

The present invention lends itself well to use with instrumentation for aligning and placing fixator pins. FIGS. 8A–8F are sectional side views of a sequence for alignment, insertion, placement, and clamping of a fixator pin in accordance with the present invention. In FIG. 8A, two pins 80 are inserted into a bone 64 on opposite ends of a fracture 62. Clamps 20 secure the pins 80 to a connecting rod 60. The pins 80 pass through soft tissue 66 and penetrate through the entire bone 64.

In FIG. 8B, a pin placing tool 70 comprising a trochar 72, an inner cannula 74 and an outer cannula 76 is slidably mounted to the connecting bar 60 with a tool clamp 78. The cannulae 74,76 are concentric with the trochar 72 (see FIG. 8B'). The tool clamp 78 may have a wider bolt hole 28A and a wider bolt hook 46 than the clamp shown in FIG. 1 to accommodate the pin placing tool. The trochar 72 advances the cannulae 74,76 through soft tissue 66 to the surface of the bone 64 at the desired angle. The tool 70 is further tightened in the clamp to prevent the outer cannula 76 from sliding away from the bone surface.

After withdrawing the trochar 70 from the inner cannula 74, a drill bit 86 is inserted therein as shown in FIG. 8C. The inner and outer cannulae 74,76 protect the soft tissues 66 from being torn or burned by the revolving drill bit 86. The drill bit 86 taps a hole 63 in the bone for the wider-diameter fixator pin 80.

In FIG. 8D, a depth gauge 88 is inserted into the inner cannula 74 and through the hole 63 in the bone 62 to determine the proper pin length for insertion. The depth gauge 88 includes a hook 89 at the distal end so that when it is inserted entirely through the bone 64, the physician can carefully tug at the pin 88 to precisely determine the opposite bone surface. The physician then measures the length at which the depth gauge was inserted and prepares a pin 20 of appropriate length.

Figure 8E:
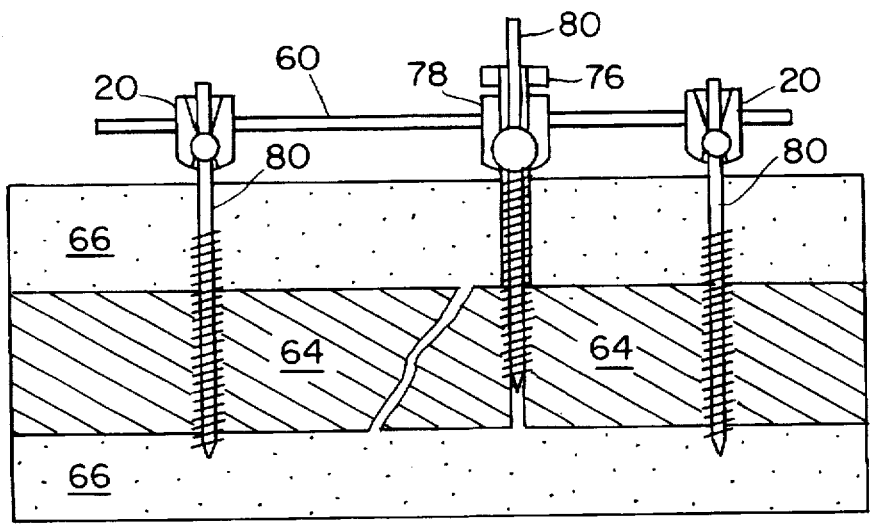
Figure 8F:
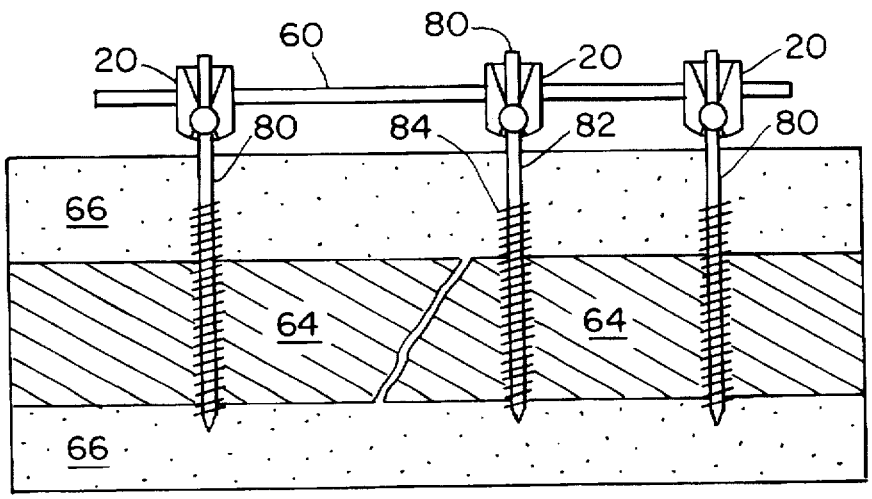

In FIG. 8E, the inner cannula 74 is removed, and a positive-profile threaded pin 20 is threaded into the hole, while the outer cannula 76 protects soft tissues 66 from being damaged by the pin 20. The pin 20 is inserted to a depth predetermined by the depth gauge 88. With the pin 20 in place, the outer cannula 76 and pin-placing clamp 78 are removed and a standard clamp 20 is attached to the connecting rod 60 and secured to the inserted pin 20 as described above. In this manner, a positive-profile pin 80 is aligned, inserted, and clamped on a connecting bar 60 between two previously-mounted pins 80 and clamps 20 as shown in FIG. 8F.

The fixator pin 80 is preferably a positive-profile threaded pin to improve pin-bone adhesion and system strength. The inner cannula 74 diameter corresponds to the diameter of the drill bit 86 used to form the pilot hole 63, and the outer cannula 76 diameter corresponds to the pin thread diameter to accommodate the positive-profile threaded pin.

Figure 9A:
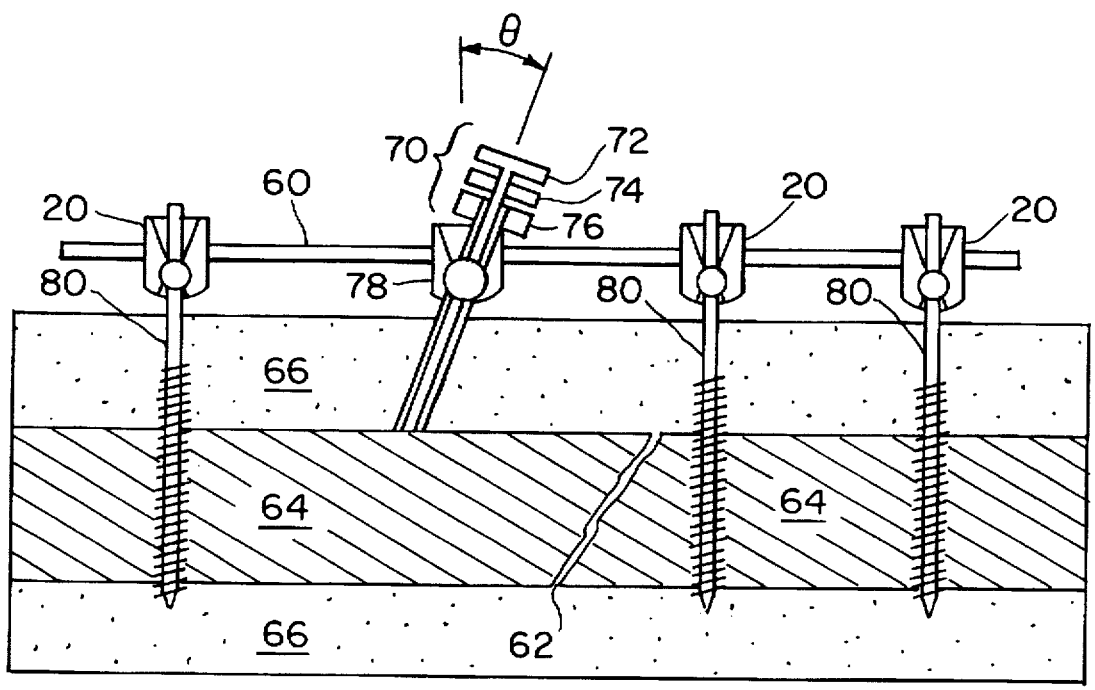
FIGS. 9A–9D are sectional side views of a tooling sequence showing angular insertion and placement of a fixator pin in accordance with the present invention.
Figure 9B:
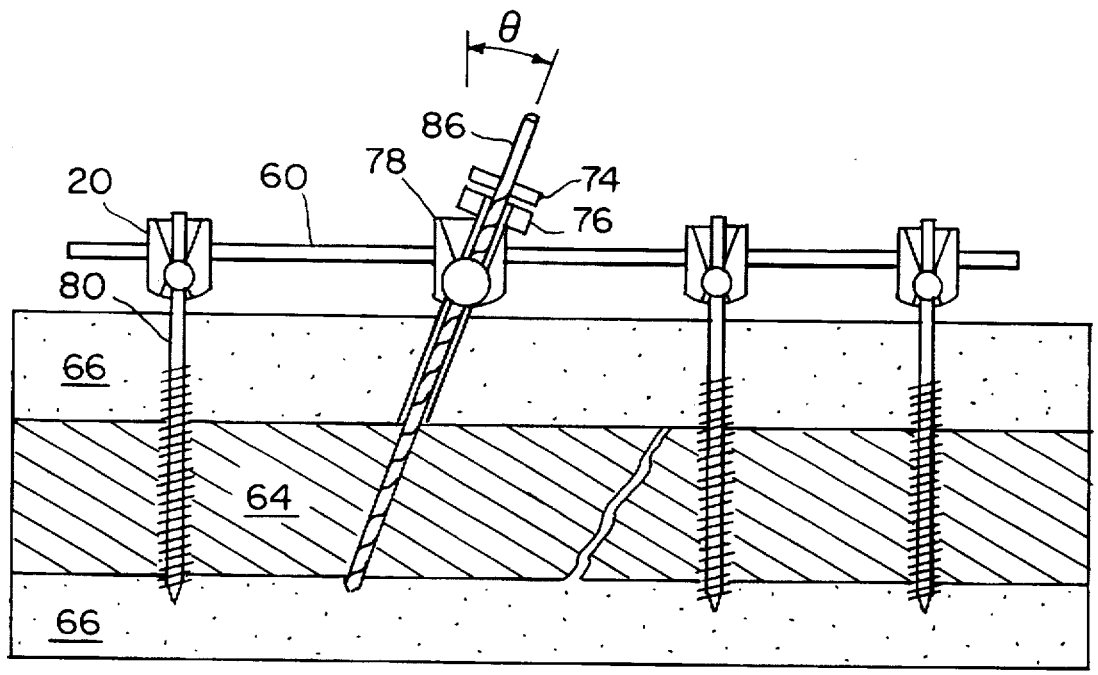
Figure 9C:
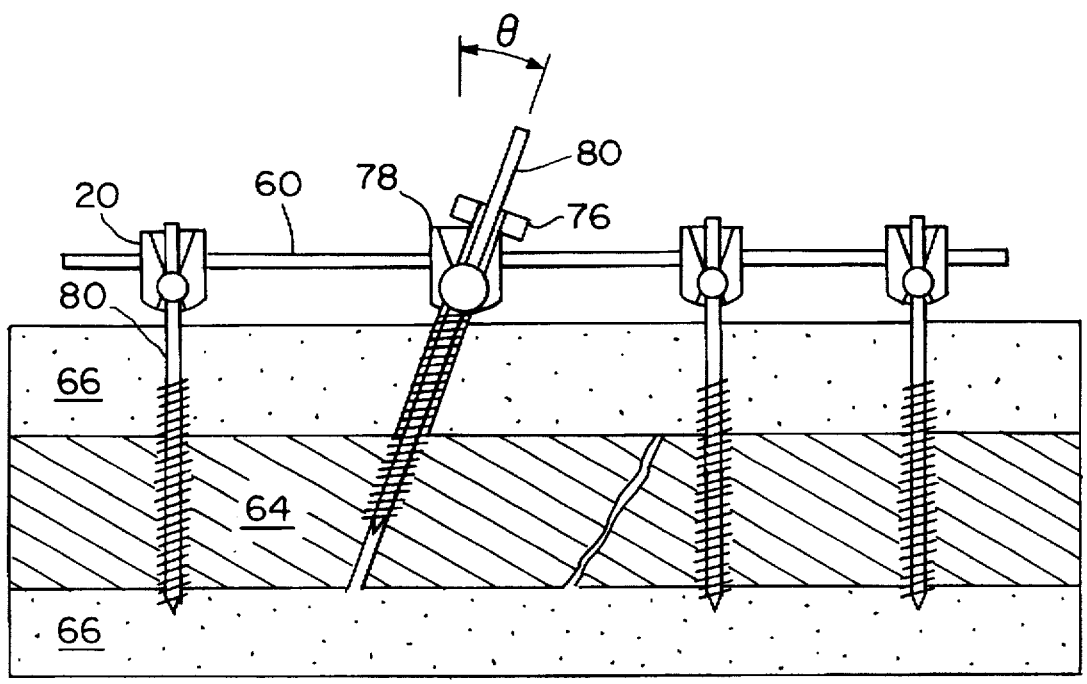
Figure 9D:
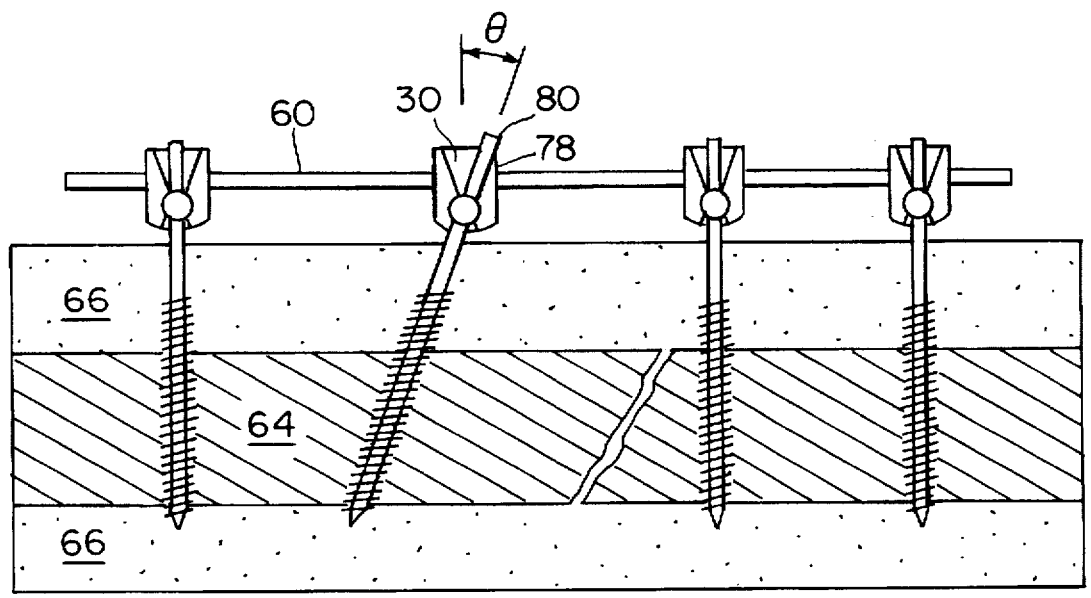

FIGS. 9A-9D are sectional top views of an instrumentation sequence showing angular insertion and placement of a fixator pin between two previously-mounted pins 80. In FIG. 9A, a pin placing tool 70 and pin placing clamp 78 are snapped on the connecting rod 60 at the side of the fracture 62 opposite that of the pin 80 placed in the sequence of FIGS. 8A-8F. The pin-placing clamp 78 is adaptable to allow the tool 70 to be rotated and aligned at an angle θ from perpendicular to the bar 60 in a manner similar to the above-described clamp 20. The trochar 72 advances the inner cannula 74 and outer cannula 76 through the soft tissue 66 to the surface of the bone 64. In FIG. 9B, the trochar 72 is removed and a drill bit 86 is inserted through the inner cannula 74 and drilled through the bone 64 with the inner and outer cannulae 74,76 protecting soft tissue 66 from the rotating drill bit 86 as described above. In FIG. 9C, the inner cannula 74 is removed and a positive-profile pin 80 is inserted through the outer cannula 76. The length of the pin 80 is predetermined by the depth gauge 88 as described above. In FIG. 9D, the pin-placing clamp 78 and outer cannula 76 are removed and replaced by a standard clamp 20 as described above. The clamp 20 includes pin grooves 30 to accommodate the angular displacement θ of the pin 80 relative to the clamp 20.

Figure 10:
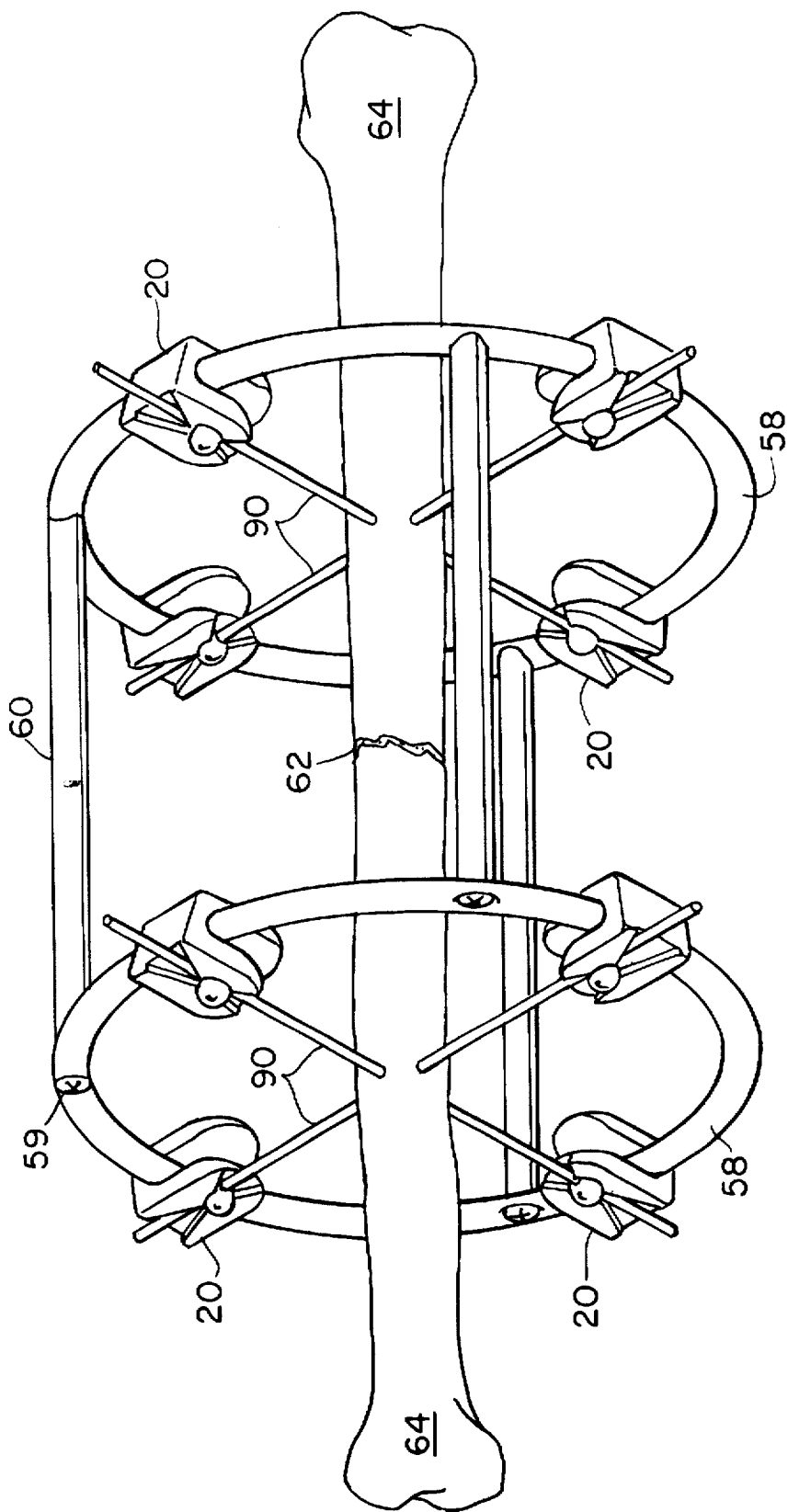
FIG. 10 is a side view of a ring fixator configuration in accordance with the present invention.

FIG. 10 is a side view of a ring fixator configuration as applied to the present invention. A plurality of rings 58 are disposed about the wounded appendage 64 as shown. Standard connecting rods 60 couple adjacent rings 58 together. Threaded bolts 59 secure the rings to the ends of the rods 60. Small diameter pins 90 are aligned and placed through the bone 64, passing through the tissue on each side of the bone 64. The pins 90 are aligned so that they are on a plane common with the ring 58. The clamps 20 snap on the ring 58 and hold the pins 90 in place. The pins 90 are preferably under tension to add additional rigidity to the structure. A ring 58 and set of pins 90 are disposed on each side of the fracture 62. The present invention is further applicable to any of the well-known frame configurations: unilateral, bilateral, triangular, quadrilateral, half-circular, circular, biplanar.

FIGS. 11A and 11B are dimensional views of prototype embodiments of the clamp 20 and bolt 30. The prototypes were built and analyzed in accordance with the stated dimensions. The prototype clamp accommodates a connecting rod 60 of 3/16 inch diameter. The prototype bolt 40 was designed for a maximum allowable torque of 80 inch-pounds. The bolt head 42 was designed to sink entirely in the bolt head hole 28A of the clamp 20 as the nut is tightened, allowing the bolt to accommodate fixator pins of less than 1/8 inch in diameter. The prototype was formed of 316 annealed stainless steel, a proven biocompatible material, to avoid tissue infection. The edges of the clamp were rounded and buffed in order to eliminate sharp or jagged edges.

During experiments performed on the prototype, at 80 inch-pounds, the bolt 40 neither deformed out of the hole nor failed. The bolt hook 46 held the pin firmly against the top 122 of the clamp 20. The bolt hole 28A deformed slightly, but not enough to prevent the clamp 20 from being reused. The lip 54 of the hook 46 did not release from the hole when the bolt was fully tightened. The stability of the system dramatically increased when the pin was aligned at plus 20° and minus 20° as a result of the pin 80 being in contact with the groove walls 32.

This now completes a description of the preferred embodiment of the invention. The following section describes a procedure for modelling and testing the clamp and bolt of FIGS. 11A and 11B. The data presented below was generated on a computer for a model designed in accordance with the dimensions given above. The dimensions given are by way of example only and the procedure outlined below is applicable to clamps and bolts of various sizes and strengths.

To accommodate transverse insertion of a connecting rod into the clamp 20, the slot 22 must be wide enough to accommodate the rod subject to a force exertable by average human hands, while producing as little deformation and stress as possible so that the clamp is reusable. Work hardening, resulting from cyclic loading must also be considered. It was determined that 316 annealed stainless steel provided adequate strength, elasticity, machinability and biocompatibility for the clamp and bolt materials. A finite element analysis of a computer model of the clamp 20 was conducted to determine the preferred slot width for the clamp so that stress was maintained within the elastic region of the clamp material (30,000 lbf/in$^2$).

To study the stress induced in the clamps 20, a computer model of the clamp 20 was generated in Aries™ Solid Modeling Software to the dimensions shown in FIG. 11A. Due to symmetry, only one side of the clamp 20 was analyzed. A finite element analysis of the model was then conducted by creating a mesh which divides the clamp into several entities. This allowed the computer to analyze the induced stress more accurately and in more locations. Translational restraints 100 were included in the model as fixed points to simulate translation about the restraints in a manner which is compatible with the forces to be analyzed. An Ansys™ analysis package conducted the force analysis.

Figure 12A:
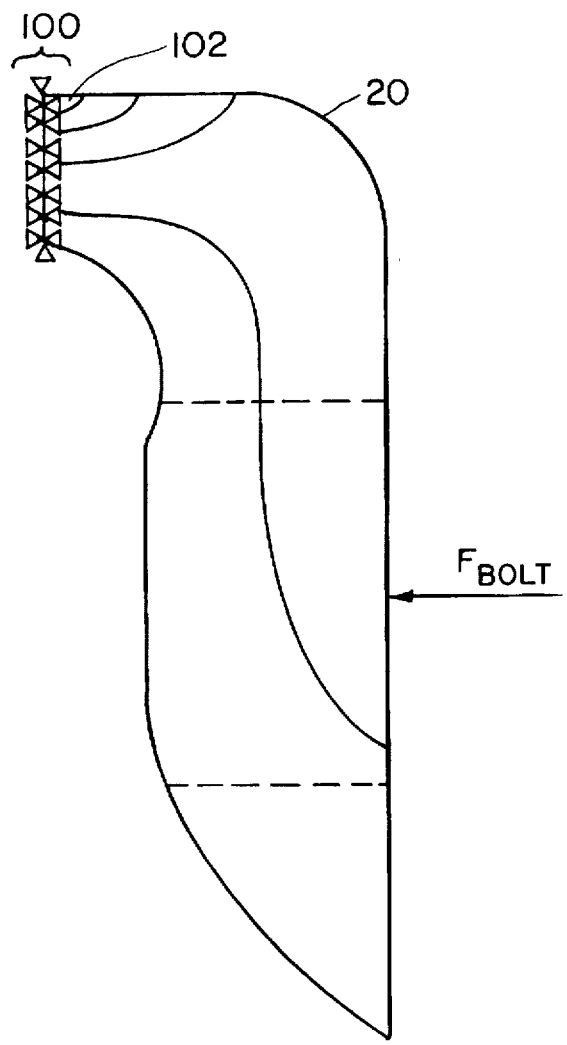
FIG. 12A is a side view of half of the clamp showing gradients of stress operating on the clamp arising from bolt tension.

The first force analyzed was $F_{Bolt}$ arising from tightening of the bolt 40 by the nut 48 as shown in FIG. 12A. For a 140 lb. load, the maximum stress induced in the clamp was approximately 69,000 lbf/in$^2$. The maximum stress for a 70 lb. load was approximately 34,500 lbf/in$^2$ and the maximum stress for a 35 lb. load was approximately 17,250 lbf/in$^2$. In all three cases, the maximum stress was on the surface of the clamp nearest the connecting rod hole in the region of gradient 102. Forces slightly smaller than approximately 70 lbs. allow the clamp to stay within the elastic region. At 70 lbs., a stress of 34,500 lbf/in$^2$ is well within the ultimate tensile strength of 75,000 lbf/in$^2$ for 314 annealed stainless steel.

Figure 12B:
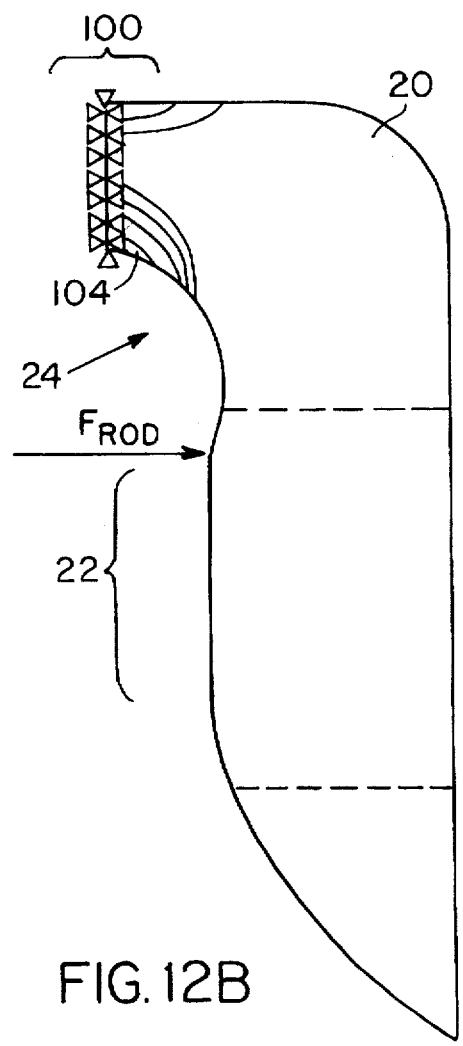
FIG. 12B is a side view of half of the clamp showing gradients of stress operating on the clamp arising from insertion of a connecting rod in the slot.

Next, the stresses associated with snapping the connecting rod 60 into the clamp 20 were analyzed. A computer model of the clamp 20 with a force $F_{Rod}$ being applied near the intersection of the connecting rod hole 24 and the slot 22 is shown in FIG. 12B. At this intersection, the force involved with inserting the rod into the slot generates the maximum outward force $F_{Rod}$ on the clamp. The analysis was conducted for slot sizes of 0.1865 inch to 0.1874 inch.

Figure 13:
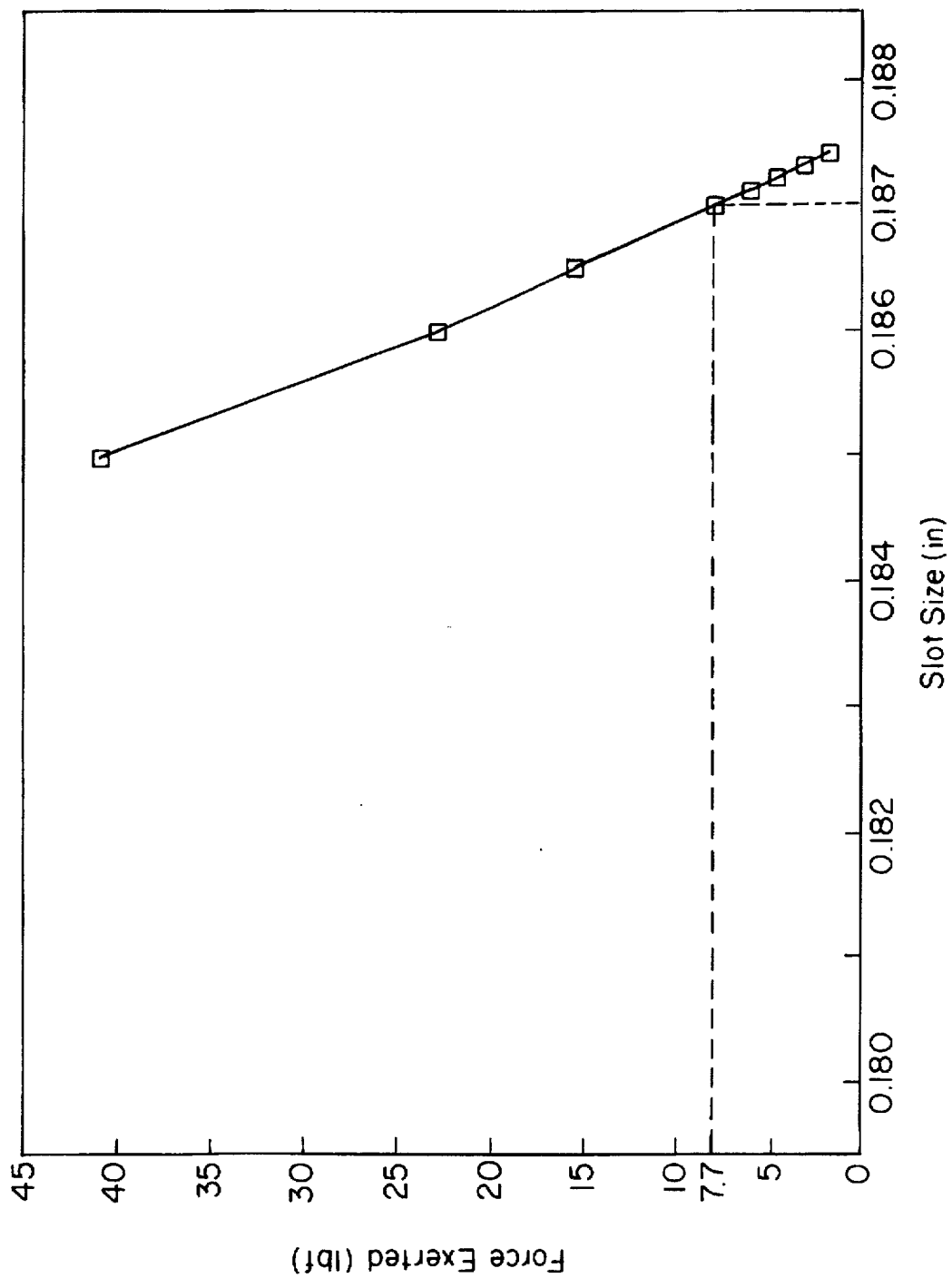
FIG. 13 is a chart of the force required for transverse insertion of a connecting rod of 0.1875 inch diameter into the clamp as a function of slot size.

FIG. 13 is a plot of the amount of force required for inserting the rod into the slot as a function of slot size. The preferred slot sizes were chosen to be those corresponding with forces attainable by human hands (15 lbf.)—between 0.1865 in. and 0.1874 in. At 0.1865 in., the force exerted to insert the rod was calculated to be 15.3 lbf. and for a slot size of 0.1874 in., the force was 1.56 lbf.

Figure 14:
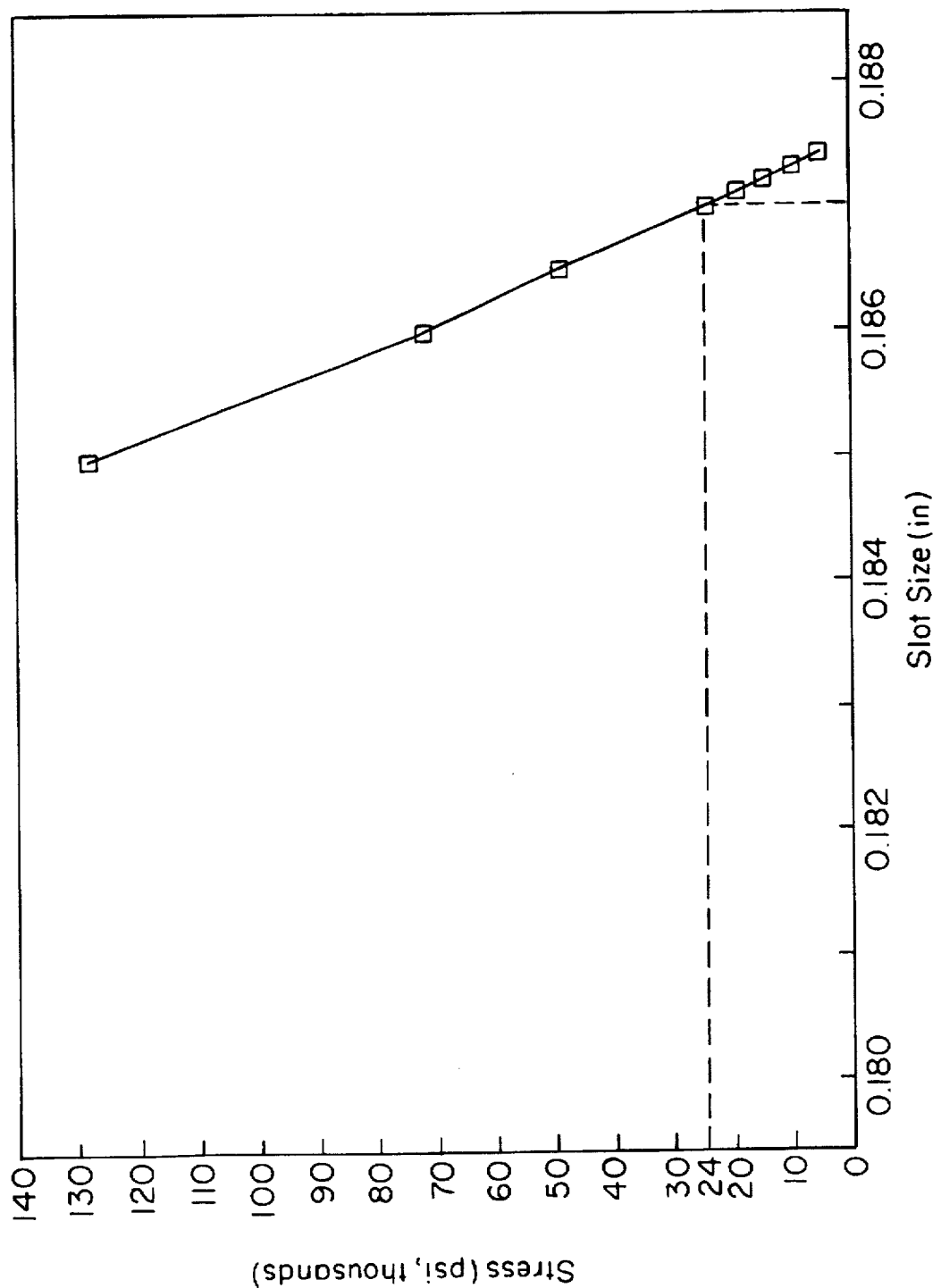
FIG. 14 is a chart of stress induced on the clamp as a function of slot size resulting from transverse insertion of a connecting rod of 0.1875 inch diameter.

The stress induced on the clamp 20 due to insertion of the rod was also considered. FIG. 14 is a plot of the stress induced as a function of slot size. For a slot size of 0.1865 in., the maximum stress induced was 48,100 lbf/in$^2$, outside the limit of elastic deformation for stainless steel. For a slot size of 0.1874 in., the stress was minimal, approximately 5,000 lbf/in$^2$. With a slot size of 0.1870 in., the force required for insertion was 8 lb. and the maximum stress is 24,000 lbf/in$^2$ which is in the elastic region for the clamp material. This slot size (0.1870 in.) provides both an acceptable force for insertion of the rod and acceptable stress within the elastic region. It was therefore used as the prototype slot size.

A two-dimensional analysis of the bolt 40 using Aries™ Concept Station software was performed in order to obtain stress and displacement distributions. When tightening the bolt 40 to the clamp 20, an axial force $F_{Axial}$ operates on the bolt. The axial force was calculated to be 2,100 lbs. using the following torque equation:

$$T = Kf_l d \tag{1}$$

where:

T=torque=80 inch-pounds;

K=torque coefficient=0.2;

d=major diameter=0.19 in.; and $f_l$=axial force.

Figure 15C:
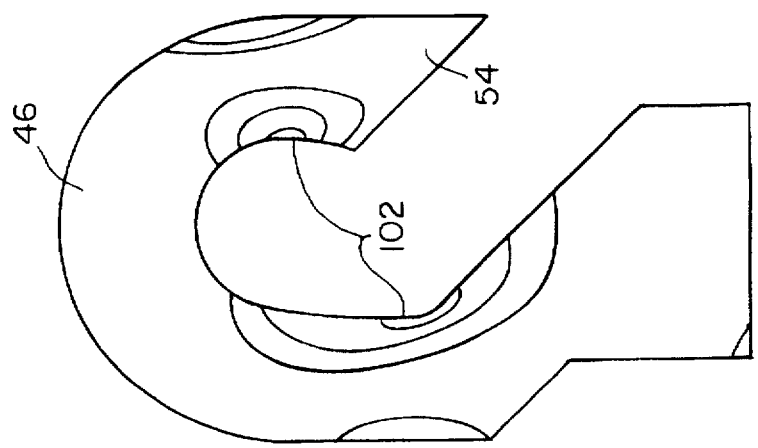
FIG. 15C shows the gradients of stress induced on the bolt hook arising from the forces of FIG. 15B.
Figure 15B:
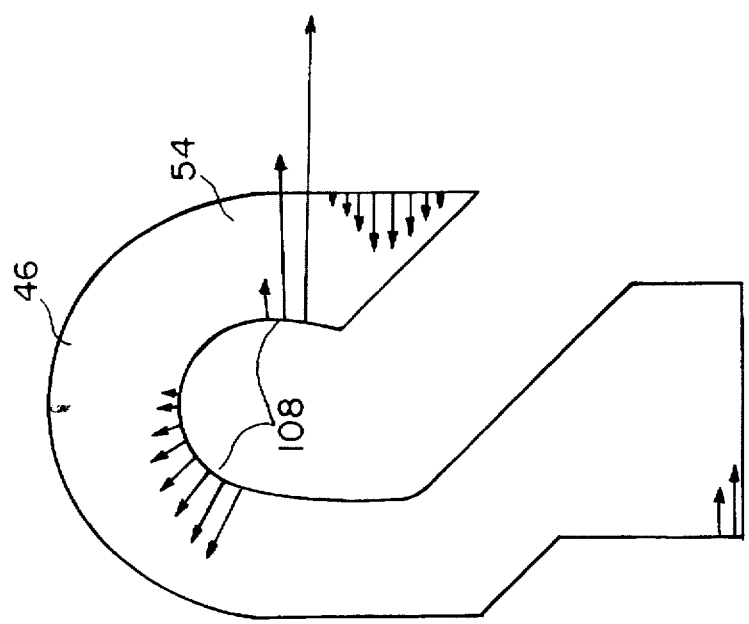
FIG. 15B is a diagram of the forces operating on the bolt hook as the bolt is tightened by the nut.
Figure 15A:
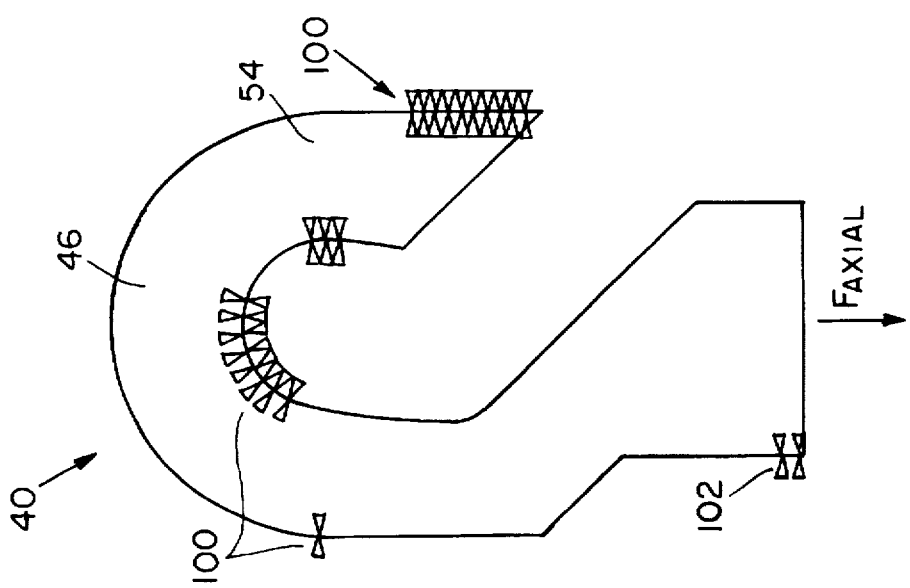
FIG. 15A is a finite point analysis computer model of a bolt hook in accordance with the present invention.

Translational restraints were added to the model as shown in FIG. 15A. A preliminary stress analysis was performed on the bolt to establish the direction of the reaction forces created on the bolt. Translational restraints having a pulling effect on the bolt were eliminated since neither the clamp nor the pin has a pulling effect on the bolt. Only translational restraints having a pushing effect were retained. The bolt was then divided into finite elements using the Aries™ Finite Element Modeling™ application to form a mesh surface of the bolt.

With a model fully prepared, a stress analysis was performed. Under the given environmental conditions, the bolt experiences multi-axial internal shear and normal stresses, represented by normal orthogonal stresses designated $\sigma_1$, $\sigma_2$, $\sigma_3$. The subscripts 1, 2, 3 represent the orthogonal coordinate axes x, y, z.

The following equation represents the Von-Mises yield criterion:

$$\tfrac{1}{2}^{1/2}[(\sigma_1-\sigma_2)^2+(\sigma_1-\sigma_3)^2+(\sigma_2-\sigma_3)^2]^{1/2}=\sigma_y \tag{2}$$

where:

$\sigma_y$=tensile yield strength, and $\sigma_1$, $\sigma_2$, $\sigma_3$=orthogonal stresses.

Since the stress analysis was two-dimensional, only the x and y coordinates were considered. Therefore, $\sigma_1$ and $\sigma_2$ were the only normal stresses used in the analysis.

The maximum stress generated in the bolt was 802,000 lbf/in$^2$, located in the region of gradient 102 when the bolt was tightened to 80 inch-pounds of torque. This produced regions in the bolt where the Von-Mises stress exceeded the tensile yield strength of 316 stainless steel (75,000 lbf/in$^2$). This would cause major deformation of the neck portion of the bolt. Although this deformation occurred, it was observed that the bolt still remained locked within the fastener. Maximum deflection of the bolt was calculated to be 4.650 in. in the positive direction and 7.720 in. in the negative direction. This assures that the bolt will not slip out of the clamp, assuming that the clamp does not deform.

The final step of the bolt analysis is the determination of the reaction forces on the bolt due to the bolt hole 28A. The forces are shown as arrows 108 in FIG. 15B, with the length of the arrow being proportional to the magnitude of the force. Reaction forces near the lip 54 of the bolt were of far greater value. Therefore, the forces operating on the lip were the focus of the study. It was necessary to calculate these forces on the side of the bolt since equal and opposite forces were experienced on the wall of the bolt hole on the 28A on the clamp 20.

A two-dimensional analysis on the clamp was performed in order to obtain the stress and displacement distribution arising from the reaction forces. This involved creating a geometric model of the portion of the clamp surrounding the bolt hole 28A as shown in FIGS. 16A and 16B. Due to the fact that the largest reaction forces were encountered in the head of the bolt, only the top half of the clamp was analyzed. Due to symmetry, the top half of the clamp was further reduced in half, simplifying the two-dimensional analysis. Translational restraints 100 in the x-direction and y-direction were placed along the axis of symmetry of the geometric model as shown in FIG. 16A. A sinusoidal load 104 represented by arrows 108, accurately depicts the load on the clamp 20 due to the bolt 40. In this distribution, the maximum load 106 was oriented perpendicular to the long axis of the pin with a gradual decrease in load as it is distributed outward. The load is distributed over 140° since only that surface of the bolt lip 54 is in contact with the wall of the bolt hole 28A.

FIG. 16A shows the resultant forces when the pin is disposed perpendicular to the connecting bar and FIG. 16B shows the resultant forces when the pin is displaced 20° relative to perpendicular. In the analysis, it was observed that the Von-Mises stresses decreased significantly as the width of the fastener W measured from the axis of symmetry increased. It was also observed that the maximum Von-Mises stresses shifted from the top portion of the fastener to the front portion of the fastener as the width W of the top increased.

In summary, the present invention offers several advantages over prior art fixation systems. The snap-on clamp permits attachment to a connecting bar between two previously-mounted clamps. The hooked bolt design permits alignment and insertion of positive-profile threaded pins. The device is easier to assemble and affords the surgeon a new dimension of flexibility during installation. The locking mechanism derived from the plastic deformation of the bolt results in a more stable configuration. The clamp is reusable, unlike the Kirschner-Ehmer clamp. In addition, manufacturing should be relatively inexpensive, due to mechanical simplicity.

The present invention offers a viable alternative to fixation devices currently used in the human and veterinary medical fields. This holds especially true for human fixation devices, as they generally tend to be significantly more complex and expensive. This easy to use, relatively inexpensive, extremely flexible, extremely stabile, and reusable fixation device is ideal for use in third world countries and on battle fields.

While this invention has been particularly shown and described with references to preferred embodiments thereof, it will be understood by those skilled in the art that various changes in form and detail may be made therein without departing from the spirit and scope of the invention as defined by the appended claims.

Certain aspects of the present invention such as the snap-on feature described above can be applied to more conventional clamp configurations such as the Synthes™ and Kirschner-Ehmer devices. For example, in the Synthes™ configuration, the reduced-width snap-on feature can be applied to the slot, and the standard Synthes™ bolt design can provide means for coupling the fixator pin to the clamp. Also, the hooked-bolt embodiment can be applied to the Kirschner-Ehmer clamp configuration.

Figure 17:
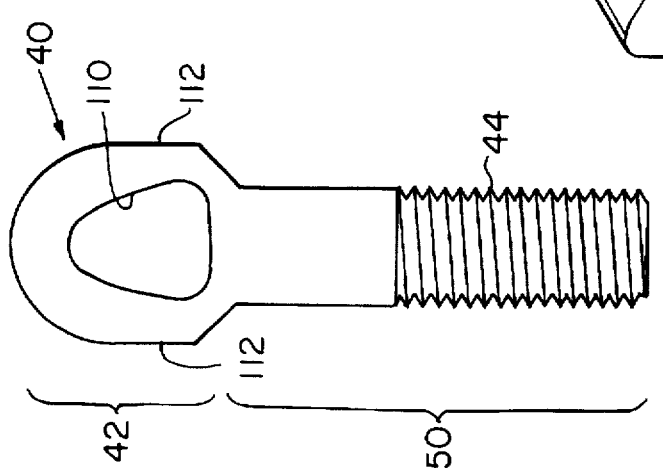
FIG. 17 is a side view of an alternative bolt embodiment having a hole for receiving a pin shaft in accordance with the present invention.

Furthermore, the bolt 40 can include a hole 110 rather than a hook in the bolt head 42 as shown in FIG. 17. The end of a pin 80 could be inserted through the hole 110 to join the pin 80 to the clamp. A closed hole does not have the advantage of the installation flexibility offered by the hook, for example, for hooking a placed pin as described above, but may provide a cost advantage where the hook is not required as the hole would be easier to manufacture. The hole may be tapered to accommodate a variety of pin diameters. In either case, the bolt is preferably adapted to deform around the pin, as described above for the hooked embodiment. The deformation causes the side walls 112 of the bolt head 42 to exert an outward force on the inner surface of the bolt hole 28A, providing torsional rigidity as described above.

FIGS. 18A and 18B are alternative clamp embodiments showing various groove configurations. In FIG. 18A, a groove 30 of diameter substantially similar to the pin is formed on the top surface 122 of the clamp 20 to provide a defined angle for pin insertion relative to the connecting bar. The example shown in FIG. 18A demonstrates orthogonal pin positioning, but single grooves may be positioned at various angles to provide for a variety of angular pin placements.

In FIG. 18B, a plurality of grooves 130 are provided to allow discrete pin displacement at predetermined angles. For example, groove 130A allows orthogonal pin placement while grooves 130B permit pin placement at plus or minus 20° relative to the orthogonal groove 130A.

Figure 19C:
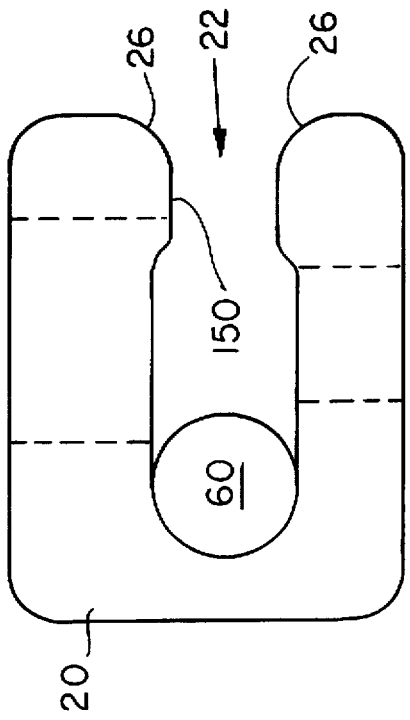
FIGS. 19A–19D are side views of various clamp slot configurations in accordance with the present invention.
Figure 19D:
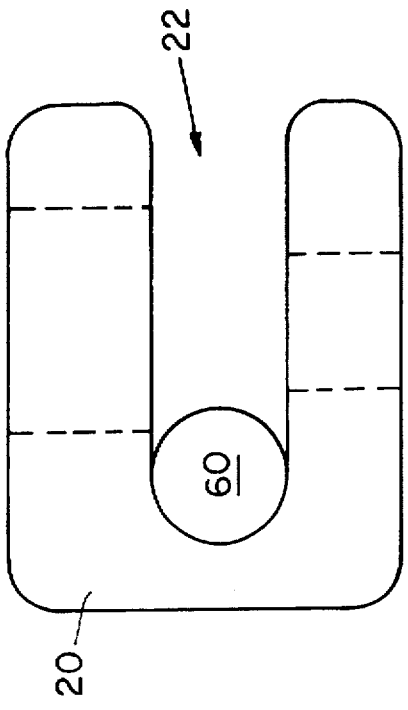
Figure 19A:
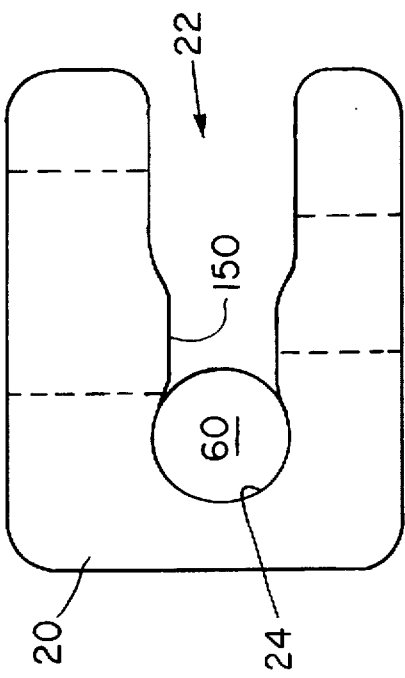
Figure 19B:
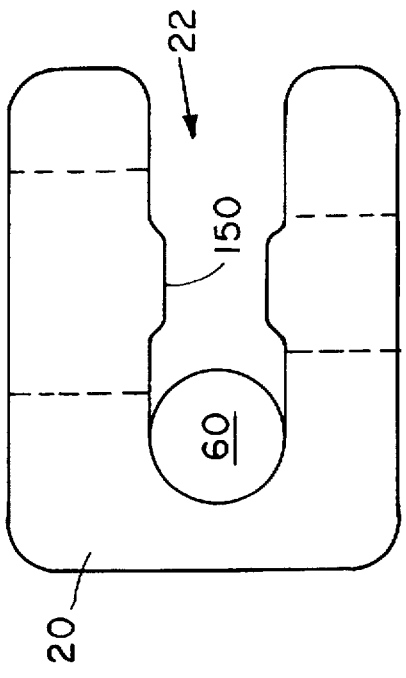

Although the clamp embodiment described above includes a slot having a region of reduced width that runs the length of the slot, other configurations are possible, including but not limited to those illustrated in FIG. 19A–D. In FIG. 19A, the region of reduced width 150 is adjacent the connecting rod channel and does not extend through the slot. The region 150 may also comprise opposed raised bumps in the middle of the slot 22 as shown in FIG. 19B. If the region 150 is near the slot opening as shown in FIG. 19C, tapered entrance surfaces 26 should be included to help guide the rod 60 into the slot opening.

FIG. 19D illustrates a clamp having a U-shaped slot with no region of reduced width. This configuration may be useful for the temporary tool clamp 78 (see FIGS. 8A–8F) where weak coupling between the clamp 20 and connecting bar 60 may be tolerable during installation of the fixator pin. This clamp 20 would be easy to remove after installation of the pin.

Furthermore, the hooked bolt embodiment described above is adaptable to a variety of clamp configurations. These configurations are not limited to those described above in conjunction with the present invention but may include the Kirschner-Ehmer and Synthes™ clamp configurations.

The components may be constructed out of a variety of materials. The material chosen must be biocompatible so as not to interfere with the healing process. It is also preferred that the material is machineable so that manufacturing costs are kept to a minimum. The material must have a relatively high modulus of elasticity and high yield strength. Failure strength should also be maximized. The clamp material should be able to deform elastically, while the material used for the bolt should deform plastically. In view of this, it is recommended that the clamp be constructed of stainless steel or carbon fiber reinforced polymers. The recommended bolt material is stainless steel because of its ability to deform plastically.

Additional details related to the design and testing of the present invention can be found in "Design of a Fastener and Bolt for an External Fixation Device" by David P. Brooks, II, Brian E. Cotton, Danielle L. Luongo, and Harold M. Wotton, III, and "External Skeletal Fixation" by George E. Chu, Brian J. Rollins and Donald M. Kallio, Jr., both submitted as Major Qualifying Projects to the faculty of Worcester Polytechnic Institute in partial fulfillment of the requirements for the degree of Bachelor of Science. Both documents are incorporated herein by reference.

We claim:

1. An external fixator clamp comprising:
    a unitary u-shaped clamp body having a slot dimensioned to transversely receive a connecting rod and a hole extending transversely through the slot; and
    a pin connector extending through the clamp body hole and having a hole for receiving a fixator pin to brace the pin against the clamp body.

2. The clamp of claim 1 wherein the pin connector comprises:
    a bolt including a thread; wherein a nut is used to retain the bolt in the hole through the clamp body.

3. The clamp of claim 1 wherein the hole in the pin connector is hook-shaped.

4. The clamp of claim 3 wherein the pin connector comprises a lip which wraps around the fixator pin shaft, the lip being deformable to exert an outward force against an inner surface of the hole in the clamp body.

5. The clamp of claim 3 wherein the pin connector undergoes plastic deformation upon tightening of the nut.

6. The clamp of claim 1 wherein compressive force exerted by the pin connector to brace the fixator pin causes only elastic deformation of the clamp body.

7. The clamp of claim 1 wherein the pin connector is rotatably mounted in the hole through the clamp body such that the pin can be secured at a range of angles relative to the connecting rod.

8. The clamp of claim 1 wherein the clamp body further comprises at least one groove having walls such that the fixator pin is secured between the pin connector and the groove within the walls of the groove.

9. The clamp of claim 1 wherein the connecting rod is ring-shaped.

10. An external fixator clamp comprising:
    a unitary u-shaped clamp body having a slot for transversely receiving a connecting rod and a hole disposed transversely to the slot;
    a nut; and a bolt including a thread and a head, the head comprising a hook for hooking a fixator pin shaft; the bolt being inserted through the hole in the clamp body, retained at the head by a fixator pin and secured at the thread by the nut.

11. The clamp of claim 10 wherein the slot includes a region of reduced width providing interference between the slot and a connecting rod transversely inserted therein.

12. The clamp of claim 10 wherein the hook comprises a lip which wraps around the fixator pin shaft, the lip being deformable to exert an outward force against an inner surface of the hole through the clamp body upon tightening of the nut.

13. The clamp of claim 10 wherein the bolt head undergoes plastic deformation upon tightening of the nut.

14. An external fixator system comprising:
    a connecting rod;
    a fixator pin;
    a unitary u-shaped clamp comprising a slot for transversely receiving the connecting rod, and a hole disposed transversely through the slot;
    a nut; and
    a bolt including a head and a thread inserted through the hole, retained at the head by the fixator pin and secured at the thread by the nut.

15. The system of claim 14 wherein the slot includes a region of reduced width providing interference between the slot and the connecting rod.

16. The system of claim 14 wherein the bolt head includes a hook for hooking the fixator pin, the hook securing the fixator pin against the clamp upon tightening of the nut.

17. The system of claim 14 wherein the bolt is rotatably mounted in the hole such that the pin can be secured at a range of angles relative to the connecting rod.

18. A method for coupling a fixator pin to a connecting rod comprising the steps of:
    forming a slot in a clamp; the slot having a region of reduced width;
    inserting the connecting rod transversely into the slot such that the connecting rod interferes with the reduced width slot region, causing the clamp to snap onto the connecting rod;
    forming a hook on a bolt head;
    hooking a fixator pin with the hook;
    inserting the bolt through a hole disposed transversely through the slot;
    retaining the head of the bolt with the fixator pin; and
    securing the bolt with a nut.

19. The method of claim 18 further comprising the step of tightening the nut such that the bolt generates a compressive force on the clamp between the nut and fixator pin, reducing the width of the slot, causing the clamp to tighten about the connecting rod.

20. The method of claim 18 further comprising the steps of:
    rotatably mounting the bolt in the hole; and
    securing the fixator pin to the clamp at an acute angle relative to the connecting rod.

21. A method for coupling a fixator pin to a connecting rod comprising the steps of:
    forming a slot having a channel for receiving a connecting rod in a clamp;
    inserting a connecting rod into the channel;
    inserting a bolt including a head and a thread through a hole disposed transversely through the slot, the bolt head comprising a hook for receiving a fixator pin;
    hooking a fixator pin with the hook, the fixator pin retaining the head of the bolt; and
    securing the thread of the bolt with the nut.

22. The method of claim 21 further comprising the step of forming a slot having a region of reduced width such that a transversely inserted connecting rod interferes with the reduced-width slot region, causing the clamp to snap onto the connecting rod.

23. The method of claim 21 further comprising the steps of:
    rotatably mounting the bolt in the hole; and
    securing the fixator pin to the clamp at an acute angle relative to the connecting rod.

24. A method for coupling a fixator pin to a connecting rod comprising the steps of:
    forming a slot in a clamp;
    inserting a connecting rod transversely into the slot;
    forming a hook on a bolt head;
    rotatably inserting the bolt through a hole disposed transversely through the slot;
    hooking the fixator pin with the hook;
    retaining the head of the bolt with the fixator pin; and
    securing the bolt with a nut.

25. The method of claim 24 further comprising the step of forming the slot with a region of reduced width such that the connecting rod interferes with the reduced-width slot region, causing the clamp to snap onto the connecting rod.

26. An instrument for installing a fixator pin comprising:
    a clamp for slidably receiving a cannula, the clamp having a slot for receiving a connecting rod transversely inserted therein; and
    a cannula slidably mounted to the clamp, the cannula being insertable through soft tissue to a bone surface, the cannula providing access to the bone for insertion of a fixator pin while protecting the soft tissue from interference with the fixator pin.

27. The instrument of claim 26 further comprising a trochar slidably inserted through the cannula for advancing the cannula to the bone surface.

28. The instrument of claim 26 further comprising a drill for drilling a pilot hole through the bone, the cannula protecting soft tissue during drilling.

29. The instrument of claim 26 further comprising a depth gauge for measuring the depth of the pilot hole.

30. The instrument of claim 26 wherein the fixator pin is a positive-profile threaded fixator pin having a thread diameter larger than a shaft diameter.

31. The instrument of claim 30 wherein the cannula comprises an inner cannula slidable within an outer cannula, the inner cannula diameter corresponding to a pilot hole drilled into the bone and the outer cannula diameter corresponding to the fixator pin thread diameter.

32. A method for installing a fixator pin comprising:
    attaching a clamp transversely on a connecting rod, the clamp being dimensioned to slidably receive a cannula;
    slidably mounting a cannula to the clamp;
    inserting the cannula through soft tissue to a bone surface; and
    inserting a fixator pin through the cannula into the bone, the cannula protecting the soft tissue from interference with the fixator pin.

33. The method of claim 32 further comprising the step of inserting a trochar into the cannula for advancing the cannula through soft tissue to the bone surface.

34. The method of claim 32 further comprising the step of drilling a pilot hole through the inserted cannula into the bone, the cannula protecting the soft tissue during drilling.

35. The method of claim 34 further comprising the step of measuring the depth of the pilot hole with a depth gauge.

36. The method of claim 32 wherein the step of inserting a fixator pin further comprises the step of inserting a positive-profile fixator pin.

37. A method for installing an external fixator pin comprising:

mounting a clamp on a connecting rod in a transverse direction;

slidably securing a pin placing tool, comprising a trochar disposed within an inner cannula and an outer cannula, to the clamp;

advancing the pin placing tool through soft tissue to the surface of a fractured bone;

removing the trochar from the inner cannula;

drilling a pilot hole through the bone with the drill bit;

removing the drill bit and inner cannula from the outer cannula;

threading a fixator pin through the outer cannula into the pilot hole;

withdrawing the outer cannula from the soft tissue; and mounting the fixator pin to a clamp.

38. The method of claim 37, wherein the step of threading the fixator pin further comprises threading a positive-profile fixator pin.

39. The method of claim 37 wherein the step of securing the pin placing tool to the clamp further comprises securing the tool to the clamp at an acute angle relative to the connecting rod.

* * * * *